(12) United States Patent
Kozikowski et al.

(10) Patent No.: US 6,180,648 B1
(45) Date of Patent: Jan. 30, 2001

(54) ANALOGS OF COCAINE

(75) Inventors: Alan P. Kozikowski, Princeton, NJ (US); Gian Luca Araldi, Washington, DC (US)

(73) Assignee: Biostream Therapeutics, Inc., Cambridge, MA (US)

(*) Notice: Under 35 U.S.C. 154(b), the term of this patent shall be extended for 0 days.

(21) Appl. No.: 09/056,727

(22) Filed: Apr. 7, 1998

Related U.S. Application Data

(60) Provisional application No. 60/042,775, filed on Apr. 7, 1997.

(51) Int. Cl.[7] .................. A61K 31/445; A61K 31/451; A61K 31/435
(52) U.S. Cl. .................. 514/317; 546/215; 546/216; 546/217; 546/184; 546/192
(58) Field of Search .................. 546/184, 192, 546/198, 205, 206, 236, 157, 207, 214, 215, 216, 217; 514/317

(56) References Cited

U.S. PATENT DOCUMENTS

| | | | | |
|---|---|---|---|---|
| 3,912,743 | * | 10/1975 | Christensen et al. | 546/197 |
| 4,007,196 | * | 2/1977 | Christensen et al. | 546/197 |
| 4,877,799 | * | 10/1989 | Drejer et al. | 514/317 |
| 5,208,232 | * | 5/1993 | Jakobsen et al. | 514/228.9 |

FOREIGN PATENT DOCUMENTS

| | | | |
|---|---|---|---|
| 2404113 | * | 8/1974 | (DE) . |
| 3441929 A1 | * | 5/1986 | (DE) . |
| 3441927 | | 5/1986 | (DE) . |
| 3441929 | | 5/1986 | (DE) . |
| 0339579 | * | 2/1989 | (EP) . |
| 0339579 | | 11/1989 | (EP) . |
| 0374674 | | 6/1990 | (EP) . |
| WO97/34602 | | 9/1997 | (WO) . |

OTHER PUBLICATIONS

Pandiarajan et al, XP–002074607, Magnetic Resonance in Chemistry vol. 31 pp. 80–89, Aug. 13, 1992.*

Chem. Abstract 92:27539, Jackobsen Palle et al. RN # 136104–98, RN# 136621–59–5,RN# 136621–60–8, Apr. 7, 1992.*

"Chemical Abstracts", vol. 109, No. 1, Beecham Group PLC, UK—Columbus, Ohio, (Jul. 4, 1988).

"Preparation of Arylpyridy carbinol derivaties as antidepressants", *Beecham Group PLC*, (1985).

"Preparation of Nicotinate ester derivatives as intermediates for antidepressants", *Chemical Abstracts*, vol. 107, No. 15 (Oct. 12, 1987).

(List continued on next page.)

*Primary Examiner*—Alan L. Rotman
*Assistant Examiner*—Rita Desai
(74) *Attorney, Agent, or Firm*—Beth E. Arnold; Dana M. Gordon; Foley, Hoag & Eliot LLP

(57) ABSTRACT

The invention provides a compound of formula (I):

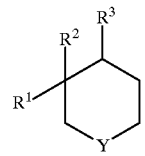

(I)

wherein $R^1$, $R^2$, $R^3$, and Y have any of the meanings defined in the specification; as well a pharmaceutical composition comprising a compound of formula I; intermediates and methods useful for preparing a compound of formula I; and therapeutic methods for treating drug addiction, Parkinson's disease or depression comprising administering a compound of formula I, to a mammal in need of such treatment.

17 Claims, 10 Drawing Sheets

OTHER PUBLICATIONS

Clarke, R.L., et al., "Compounds Affecting the Central Nervous System.4.3B–Phenyltropane–2–carboxylic Esters and Analogs", *Journal of Medicinal Chemistry*, voll. 16, No. 11, pp. 1260–1267, (1973).

Clarke, R.L., et al., "In pursuit of analgetic agents.Hydro–1, 3–ethanoindeno[2,1–c}pyridines and homologs", *Journal of Medicinal Chemistry*, vol. 17, No. 10, pp. 1040–1046, (1974).

Engestoft, M., et al., "Synthesis and 5HT modulating activity of stereoisomers of 3–phenoxymethyl–4– phenylpiperidines", *Acta Chemica Scandinavica*, vol. 50, pp. 164–169, (1996).

Kozikowski, A.P., et al., "Chemistry and pharmacology of the piperidine–based analogues of cocaine. Identification of potent DAT inhibitors lacking the tropane skeleton", *J. Med. Chem.*, vol. 41, pp. 1962–1969, (1998).

Lambrecht, G., et al., "Structure–activity relations of substituted aromatic piperidine derivatives.1.Esters of 4–phenyldihydroarecaidine", *Arch. Pharm. (Weinheim, Germany)*, (1975).

Pandiarajan, K., et al., "Assignment of the configuration of a substituent in saturated six–membered ring compounds using the 13C chemical shifts of a single epimer", *Magnetic Resonance in Chemistry*, vol. 31, pp. 80–80, (1993).

Reith, M.E., et al., "Structural requirements for cocaine congeners to interact with '3H!batrachotoxinin in 20–.alpha.– benzoate binding sites on sodium channels in mouse brain synaptosomes", *J. Biol. chem*, (1986).

Reith, M.E., et al., "Structure activity relationships for cocaine congeners in inhibiting dopamine uptake into rat brain synaptic vesciles and bovine chromaffin granule ghosts", *The Journal of Pharmacology and Experimental Therapeutics*, vol. 271, No. 3, pp. 1444–1452, (1994).

Willcocks, K., et al., "The synthesis of [14C]–3S, 4R–(4–fluorophenyl)–=3–(3,4–methylenedioxyphenoxymethyl)piperidine hydrochloride (BRL 29060A), and mechanistic studies using carbon–13 labeling", *J. Labelled Compd. Radiopharm.*, vol. 33, No. 8, pp. 783–794, (1993).

\* cited by examiner

ANALOGS OF COCAINE

PRIORITY OF INVENTION

This application claims priority under 35 U.S.C. §119(e) from U.S. Provisional Patent Application Ser. No. 60/042,775, filed Apr. 7, 1997.

GOVERNMENT FUNDING

The invention described herein was made with U.S. Government support under grant DA11546 awarded by the National Institutes of Health, National Institute on Drug Abuse.

BACKGROUND OF THE INVENTION

Cocaine abuse is one of the greatest concerns of the American public today, and has therefore become a focus of medical, social and political leaders. Cocaine is one of the most addictive substances known, and addicts may lose their ability to function at work or in interpersonal situations. Drug dependence and the great profits that are made throughout the distribution network of cocaine have fueled a rise in drug-associated crime in the United States and in Colombia. Although the incidence of casual cocaine use has decreased substantially in the last few years, the number of weekly users is rising. The rise has accompanied a change in the chemical form often used to free base, or "crack," and the route of administration used from nasal to inhalation by smoking or intravenous injection.

Psychological and behavioral approaches are important in a treatment program because peer pressure and environmental cues are closely associated with a relapse to addiction. However, behavioral observations have identified a window of about ten weeks after cessation of cocaine use where the susceptibility to relapse is greatest. Clearly, there is a need to increase the success rate of outpatient detoxification programs through the development of pharmacological agents that will assist during this critical period.

Currently a number of treatment strategies are being looked at using CNS agents developed for other indications. The agents being tried include, among others, the indirect dopamine agonist, amantadine, the direct agonist bromocriptine, the partial mu opiate receptor agonist, buprenorphine, and the tricyclic antidepressant, desipramine. While these agents appear to depress either self-administration or cocaine "craving" under certain circumstances, these studies are still in their early stages and the efficacy of such treatments has not been established.

The behavioral properties of cocaine, including its abilities to act as a reinforcer, are thought to stem from its ability to inhibit the reuptake of dopamine (DA). While cocaine also has the ability to act as an inhibitor of serotonin and norepinephrine uptake as well as to bind to sigma opiate and muscarinic receptors, the potencies of cocaine and analogs in self-administration studies correlate best with their DA transporter inhibitor activities. Unfortunately, the precise mechanism by which cocaine inhibits dopamine uptake is still uncertain. Several laboratories have shown that cocaine inhibition of dopamine uptake into striatal synaptosomes is consistent with a classic, fully competitive mechanism. However these data are also consistent with more complex models, including allosteric or partially competitive, and several others involving steric hindrance, distinct but overlapping sites or multiple binding sites in which at least one is required for both cocaine and dopamine binding. In addition, a recent study using rotating disk electrode voltammetry, which is capable of monitoring uptake with a 50 msec resolution, suggests that cocaine inhibits dopamine uptake uncompetitively while competitively blocking Na$^+$ and Cl$^-$ binding to the carrier. While these data have not been validated using other experimental approaches, they further support the idea that the cocaine and dopamine binding sites are unique.

N-Ethylmaleimide (NE) is capable of inhibiting about 95% of the specific binding of [$^3$H]mazindol, and the effect of 10 mM N-ethylmaleimide is completely prevented by 10 $\mu$M cocaine, while neither 300 $\mu$M dopamine nor d-amphetamine afforded any significant protection. Furthermore, a recent study of the structure of the dopamine transporter revealed that aspartate and serine residues lying within the first and seventh hydrophobic putative membrane spanning regions were critical for dopamine uptake, but less so for [$^3$H]CFT (WIN-35428) binding. For example, replacement of the serine residues at positions 356 and 359 in the seventh hydrophobic region by alanine or glycine reduced [$^3$H]DA uptake, whereas [$^3$H]CFT (WIN-35428) binding was less affected. More recent experiments with DA and NE transporter chimeras show that transmembrane domains 6–8 determine cocaine binding while domains 9–12 plus the carboxy tail are responsible for DA binding affinity. Thus, these data support the hypothesis that a significant portion of the cocaine binding domain on the dopamine transporter is distinct from that of either dopamine or amphetamine. This distinction may be sufficient to allow properly designed drugs to prevent cocaine binding without inhibiting dopamine uptake.

The most promising agents for treating cocaine abuse, may be agents which possess the ability to mimic partially the effects of cocaine, thereby helping to maintain individuals in treatment programs while they slowly withdraw from cocaine. Such an agent would function like methadone, a drug widely used in the treatment of opiate abuse. A compound with methadone-type activity against cocaine abuse is likely to be a partial agonist of cocaine; namely, a substance that elicits some of the same effects in the user as cocaine itself, but without causing the same degree of euphoria. Ideally, the compound should have little or no abuse liability.

Thus there is currently a need for therapeutic agents that can be used to treat cocaine abuse.

SUMMARY OF THE INVENTION

The present invention provides a compound of formula (I):

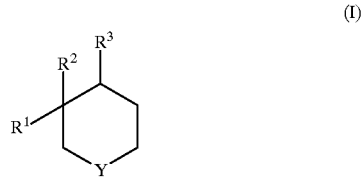

(I)

wherein

Y is NR$^6$, —C(R$^4$)(R$^5$)—, or —O—;

R$^1$ is —C(=O)OR$_a$, cyano, (C$_1$–C$_6$)alkyl, (C$_1$–C$_6$) alkanoyl, (C$_2$–C$_6$)alkenyl, (C$_2$–C$_6$)alkynyl, or 1,2,4-oxadiazol-5-yl optionally substituted at the 3-position by W, wherein any (C$_1$–C$_6$)alkyl, (C$_1$–C$_6$)alkanoyl, (C$_2$–C$_6$)alkenyl, or (C$_2$–C$_6$)alkynyl may optionally be substituted by 1, 2 or 3 Z, wherein each Z is independently halo, nitro, cyano, hydroxy, (C$_1$–C$_6$)alkoxy, $(C_2-C_6)$acyloxy, $C(=O)OR_b$, $C(=O)NR_cR_d$, $NR_eR_f$, or $S(=O)_nR_g$; and $R^3$ is $(C_6-C_{10})$aryl, 5–10 membered heteroaryl, $(C_6-C_{10})$aryl$(C_1-C_6)$alkyl, 5–10 membered heteroaryl$(C_1-C_6)$alkyl, $(C_6-C_{10})$arylcarbonyl, or 5–10 membered heteroarylcarbonyl, wherein any aryl or heteroaryl substituent may optionally be substituted on carbon by 1, 2 or 3 Z; or $R^1$ is —CH$_2$—, or —CH$_2$CH$_2$—, wherein $R^1$ is attached to a carbon at the ortho position of $R^3$; and $R^3$ is $(C_6-C_{10})$aryl, or 5–10 membered heteroaryl;

$R^2$ is hydrogen or $(C_1-C_6)$alkyl;

$R^4$ and $R^5$ are independently hydrogen or $(C_1-C_6)$alkyl;

$R^6$ is hydrogen, $(C_1-C_6)$alkyl, $(C_1-C_6)$alkanoyl, or $S(O)_2 R_h$;

n is 0, 1 or 2;

W is $(C_1-C_6)$alkyl, or phenyl, optionally substituted by 1, 2, or 3 Z;

$R_a$ to $R_g$ are independently hydrogen or $(C_1-C_6)$alkyl; and $R_h$ is H, $(C_1-C_6)$alkyl, or phenyl; or a pharmaceutically acceptable salt thereof.

Unexpectedly, it has been found that compounds of formula (I) can bind to the cocaine recognition site with an affinity comparable to that of cocaine; additionally, the compounds also act as potent inhibitors of dopamine uptake. It has been observed in drug discrimination studies in rats, that such compounds exhibit only weak cocaine- and amphetamine-like effects. The compounds of the invention thus appear to partially mimic cocaine's discriminative stimulus effects. Of further note are the results obtained from intravenous drug self-administration studies carried out using rats. In these studies, the animals trained to self-administer cocaine failed to self-administer the present compounds. In locomotor activity studies the compounds were found to have weak motor stimulant effects. Compounds with these properties may be useful for treating drug abuse or for treating disorders wherein modulation of dopamine or serotonin uptake is desired.

The invention also provides a pharmaceutical composition comprising a compound of formula I as described herein; or a pharmaceutically acceptable salt thereof; in combination with a pharmaceutically acceptable diluent or carrier.

The invention also provides a method comprising treating drug (e.g. cocaine) addiction in a human by administering a pharmaceutically effective dose of a compound of formula I; or a pharmaceutically acceptable salt thereof.

The invention also provides a method for treating a disease or condition in a mammal in which the activity of dopamine or serotonin is implicated and modulation of dopamine or serotonin reuptake is desired (e.g. Parkinson's disease or depression), comprising administering a compound of formula I; or a pharmaceutically acceptable salt thereof.

The invention also provides a compound of formula I; or a pharmaceutically acceptable salt thereof; for use in medical therapy or diagnosis.

The invention also provides the use of a compound of formula I; or a pharmaceutically acceptable salt thereof; to prepare a medicament useful for treating drug (e.g. cocaine) addiction, Parkinson's disease, or depression.

The invention also provides a radiolabeled compound comprising a radionuclide and a compound of formula I; or a pharmaceutically acceptable salt thereof, as well as methods for using such a radiolabeled compound as an imaging agent (e.g. to identify, or evaluate the function of, neurotransmitter binding sights in the brain of a mammal, such as a human).

The invention also provides a method comprising binding a compound of formula I to mammalian tissue comprising dopamine receptors, in vivo or in vitro, by contacting said tissue with an amount of a compound of formula I effective to bind to said receptors. Tissue comprising dopamine receptors with compounds of formula I bound thereto can be used as a pharmacologic tool to identify potential therapeutic agents for the treatment of diseases or conditions associated with dopamine function, by contacting the agents with the tissue, and measuring the extent of displacement of the compound of formula I and/or binding of the agent. Tissue comprising dopamine receptors with compounds of formula I bound thereto can also be used generally to elucidate the physiological function of neurotransmitters.

DETAILED DESCRIPTION OF THE INVENTION

Figure 1:
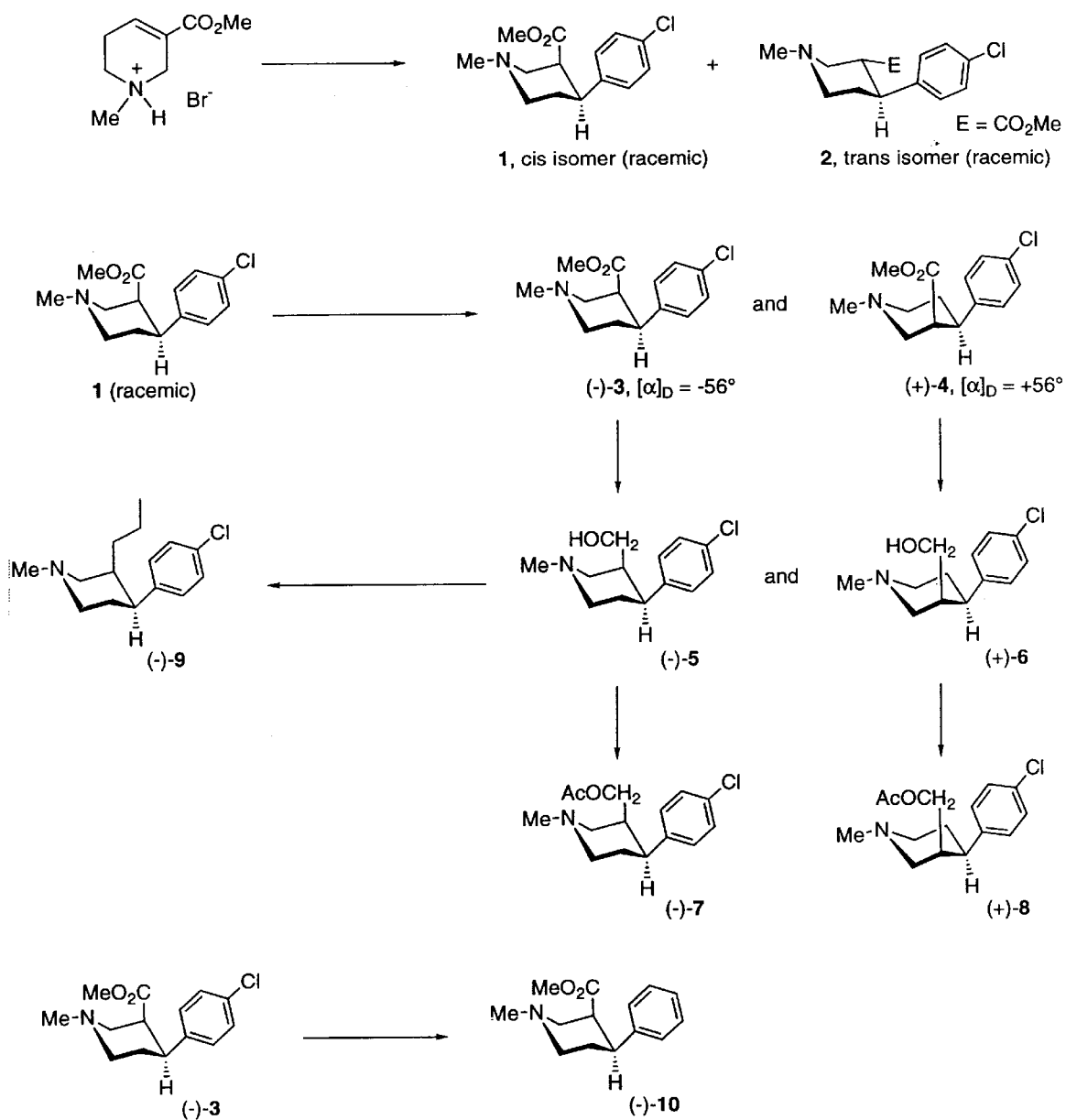
FIGS. 1–10 Illustrate the synthesis of representative compounds of the invention.

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$ alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis, from optically active starting materials, by chiral synthesis, or by chromatographic separation using a chiral stationary phase) and how to determine the relevant pharmacological properties of the compound using the standard tests described herein, or using other similar tests which are well known in the art.

Specific values listed below for radicals, substituents, and ranges, are for illustration only and they do not exclude other defined values or other values within defined ranges for the radicals and substituents Specifically, $(C_1-C_6)$alkyl can be methyl, ethyl, propyl, isopropyl, butyl, iso-butyl, sec-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexoxy; $(C_2-C_6)$alkenyl can be vinyl or allyl; $(C_2-C_6)$alkynyl can be ethynyl, 1-propynyl, or 3-propynyl;

($C_1$–$C_6$)alkanoyl can be acetyl, propanoyl or butanoyl; ($C_2$–$C_6$)acyloxy can be acetoxy, ethylcarbonyloxy or propylcarbonyloxy. Likewise, aryl can be phenyl, indenyl, or naphthyl. Heteroaryl can be furyl, imidazolyl, tetrazolyl, pyridyl, (or its N-oxide), thienyl, pyrimidinyl (or its N-oxide), indolyl, or quinolyl (or its N-oxide).

A specific value for Y is $NR_6$; wherein $R^6$ is hydrogen, ($C_1$–$C_6$)alkyl or ($C_1$–$C_6$)alkanoyl.

A specific value for $R^1$ is ($C_1$–$C_6$)alkyl, which may optionally be substituted by 1, 2 or 3 Z. Another specific value for $R^1$ is —C(=O)$OR_a$, cyano, ($C_1$–$C_6$)alkyl, ($C_1$–$C_6$) alkanoyl, ($C_2$–$C_6$)alkenyl, ($C_2$–$C_6$)alkynyl, or 1,2,4-oxadiazol-5-yl optionally substituted at the 3-position by W. Another specific value for $R^1$ is cyano, ($C_1$–$C_6$)alkyl, ($C_1$–$C_6$)alkanoyl, ($C_2$–$C_6$)alkenyl, ($C_2$–$C_6$)alkynyl, or 1,2,4-oxadiazol-5-yl optionally substituted at the 3-position by W. Another specific value for $R^1$ is ($C_1$–$C_6$)alkyl, ($C_2$–$C_6$)alkenyl, or ($C_2$–$C_6$)alkynyl. Another specific value for $R^1$ is —C(=O)$OR_a$; wherein $R_a$ is ($C_1$–$C_4$)alkyl.

A specific value for $R^2$ is hydrogen.

A specific value for $R^3$ is benzyl, wherein the phenyl ring may optionally be substituted on carbon by 1, 2 or 3 Z. Another specific value for $R^3$ is phenethyl, wherein the phenyl ring may optionally be substituted on carbon by 1, 2 or 3 Z. Another specific value for $R^3$ is 5–10 membered heteroaryl, or 5–10 membered heteroaryl($C_1$–$C_6$)alkyl, wherein any heteroaryl substituent may optionally be substituted on carbon by 1, 2 or 3 Z. Another specific value for $R^3$ is ($C_6$–$C_{10}$)aryl, ($C_6$–$C_{10}$)aryl($C_1$–$C_6$)alkyl, or ($C_6$–$C_{10}$)arylcarbonyl, wherein any aryl substituent may optionally be substituted on carbon by 1, 2 or 3 Z.

Specifically $R^4$ and $R^5$ are each independently hydrogen.

A specific value for $R^6$ is hydrogen, ($C_1$–$C_6$)alkyl or ($C_1$–$C_6$)alkanoyl. Another specific value for $R^6$ is methyl or ethyl. Another specific value for $R^6$ is hydrogen.

A specific value for $R_a$ is methyl or ethyl.

A specific group of compounds are compounds of formula I wherein $R^1$ is 2,4-oxadiazol-5-yl, optionally substituted at the 3-position by W.

Another specific group of compounds are compounds of formula I wherein $R^1$ is —C(=O)$OR_a$, cyano, ($C_1$–$C_6$)alkyl, ($C_1$–$C_6$)alkanoyl, ($C_2$–$C_6$)alkenyl, ($C_2$–$C_6$)alkynyl, or 1,2,4-oxadiazol-5-yl optionally substituted at the 3-position by W, wherein any ($C_1$–$C_6$)alkyl, ($C_1$–$C_6$)alkanoyl, ($C_2$–$C_6$) alkenyl, or ($C_2$–$C_6$)alkynyl may optionally be substituted by 1, 2 or 3 Z, wherein each Z is independently nitro, cyano, ($C_1$–$C_6$)alkoxy, ($C_2$–$C_6$)acyloxy, C(=O)$OR_b$, C(=O)$NR_cR_d$, or S(=O)$_nR_g$; and $R^3$ is ($C_6$–$C_{10}$)aryl, 5–10 membered heteroaryl, ($C_6$–$C_{10}$)aryl($C_1$–$C_6$)alkyl, 5–10 membered heteroaryl($C_1$–$C_6$)alkyl, ($C_6$–$C_{10}$)arylcarbonyl, or 5–10 membered heteroarylcarbonyl, wherein any aryl or heteroaryl substituent may optionally be substituted on carbon by 1, 2 or 3 Z; or $R^1$ is —$CH_2$—, or —$CH_2CH_2$—, wherein $R^1$ is attached to a carbon at the ortho position of $R^3$; and $R^3$ is ($C_6$–$C_{10}$)aryl, or 5–10 membered heteroaryl; or a pharmaceutically acceptable salt thereof, provided that $R^3$ is not phenyl, when $R^1$ is methoxycarbonyl or acetoxymethyl, $R^2$ is hydrogen, Y is $NR^6$, and $R^6$ is methyl.

Another specific group of compounds are compounds of formula I wheren $R^1$ is —C(=O)$OR_a$, cyano, ($C_1$–$C_6$)alkyl, ($C_1$–$C_6$)alkanoyl, ($C_2$–$C_6$)alkenyl, ($C_2$–$C_6$)alkynyl, or 1,2,4-oxadiazol-5-yl optionally substituted at the 3-position by W, wherein any ($C_1$–$C_6$)alkanoyl, ($C_2$–$C_6$)alkenyl, or ($C_2$–$C_6$)alkynyl may optionally be substituted by 1, 2 or 3 Z, wherein each Z is independently halo, nitro, cyano, hydroxy, ($C_1$–$C_6$)alkoxy, ($C_2$–$C_6$)acyloxy, C(=O)$OR_b$, C(=O)$NR_cR_d$, $NR_eR_f$, or S(=O)$_nR_g$; and $R^3$ is ($C_6$–$C_{10}$)aryl, 5–10 membered heteroaryl, ($C_6$–$C_{10}$)aryl($C_1$–$C_6$)alkyl, 5–10 membered heteroaryl($C_1$–$C_6$)alkyl, ($C_6$–$C_{10}$)arylcarbonyl, or 5–10 membered heteroarylcarbonyl, wherein any aryl or heteroaryl substituent may optionally be substituted on carbon by 1, 2 or 3 Z; or $R^1$ is —$CH_2$—, or —$CH_2CH_2$—, wherein $R^1$ is attached to a carbon at the ortho position of $R^3$; and $R^3$ is ($C_6$–$C_{10}$)aryl, or 5–10 membered heteroaryl; or a pharmaceutically acceptable salt thereof, provided that $R^3$ is not phenyl, when $R^1$ is methoxycarbonyl, $R^2$ is hydrogen, Y is $NR^6$, and $R^6$ is methyl.

Another specific group of compounds are compounds of formula I wheren Y is —C($R^4$)($R^5$)—, or —O—; or a pharmaceutically acceptable salt thereof.

Another specific group of compounds are compounds of formula I wheren $R^1$ is —C(=O)$OR_a$, cyano, ($C_1$–$C_6$)alkyl, ($C_1$–$C_6$)alkanoyl, ($C_2$–$C_6$)alkenyl, ($C_2$–$C_6$)alkynyl, or 1,2,4-oxadiazol-5-yl optionally substituted at the 3-position by W; and $R^3$ is ($C_6$–$C_{10}$)aryl, 5–10 membered heteroaryl, ($C_6$–$C_{10}$)aryl($C_1$–$C_6$)alkyl, 5–10 membered heteroaryl ($C_1$–$C_6$)alkyl, ($C_6$–$C_{10}$)arylcarbonyl, or 5–10 membered heteroarylcarbonyl, wherein any aryl or heteroaryl substituent may optionally be substituted on carbon by 1, 2 or 3 Z; or $R^1$ is —$CH_2$—, or —$CH_2CH_2$—, wherein $R^1$ is attached to a carbon at the ortho position of $R^3$; and $R^3$ is ($C_6$–$C_{10}$) aryl, or 5–10 membered heteroaryl; or a pharmaceutically acceptable salt thereof; provided that $R^3$ is not phenyl, when $R^1$ is methoxycarbonyl, $R^2$ is hydrogen, Y is $NR_6$, and $R^6$ is methyl.

A specific group of compounds are compounds of formula I wherein $R^1$ is —C(=O)$OR_a$, cyano, ($C_1$–$C_6$)alkyl, ($C_1$–$C_6$)alkanoyl, ($C_2$–$C_6$) alkenyl, or ($C_2$–$C_6$)alkynyl, wherein any ($C_1$–$C_6$)alkyl, ($C_1$–$C_6$)alkanoyl, ($C_2$–$C_6$) alkenyl, or ($C_2$–$C_6$)alkynyl may optionally be substituted by 1, 2 or 3 Z, wherein each Z is independently halo, nitro, cyano, hydroxy, ($C_1$–$C_6$)alkoxy, ($C_2$–$C_{10}$)acyloxy, C(=O)$OR_b$, C(=O)$NR_cR_d$, $NR_eR_f$, or S(=O)$_n$, $R_g$; and $R^3$ is phenyl which may optionally be substituted on carbon by 1, 2 or 3 Z.

A preferred value for $R^3$ is 4-chlorophenyl, 4-fluorophenyl, 4-methylphenyl, or 4-isopropenylphenyl.

A preferred group of compounds are compounds of formula I wherein $R^1$ and $R^3$ are in a trans configuration.

A preferred group of compounds are compounds of formula I wherein Y is $NR^6$; $R^1$ is methoxycarbonyl, ($C_1$–$C_6$) alkyl, or acetoxymethyl; $R^2$ is hydrogen; and $R^3$ is 4-chlorophenyl, 4-fluorophenyl, 4-methylphenyl, or 4-isopropenylphenyl; and $R^6$ is methyl; or a pharmaceutically acceptable salt thereof.

A preferred compound is (+)-methyl 4β-(4-chlorophenyl)-1-methylpiperidine-3α-carboxylate; or a pharmaceutically acceptable salt thereof.

Another preferred compound is (−) 4β-(4-chlorophenyl)-1-methyl-3β-n-propylpiperidine; or (+) 4β-(4-chlorophenyl)-1-methyl-3α-n-propylpiperidine; or a pharmaceutically acceptable salt thereof.

Processes and intermediates useful for preparing; compounds of formula I are provided as further embodiments of the invention and are illustrated by the following procedures.

As illustrated in FIG. 1, racemic piperidines 1 and 2 were prepared starting from arecoline hydrobromide using chemistry similar to that reported by Plati for the synthesis of the unsubstituted phenyl bearing piperidine analogs (Plati, J. T.;

Ingberman, A. K.; Wenner, W. Pyrilindene Derivatives. III. Synthesis from Arecoline. *J. Org. Chem.* 1957, 22, 261–265).

Thus, the hydrobromide salt of arecoline was converted to its free base by sodium bicarbonate, and this intermediate subjected to a Grignard reaction using p-chlorophenylmagnesium bromide. A mixture of the cis- and trans-disubstituted piperidines 1 and 2 was produced in a 75/25 ratio. The cis derivative was obtained by crystallization of the crude material using EtCAc/hexane as solvent. The racemic trans piperidine was readily obtained by flash chromatography of the mother liquor.

The cis ester was resolved by use of (+)- and (–)-dibenzoyltartaric acid to provide the pure enantiomers (–)-3 and (+)-4 (Law, H.; Leclerc, G. A.; Neumeyer, J. L. An efficient and inexpensive resolution of the potent dopaminergic substance 3-(3-Hydroxyphenyl)-N-(1-propyl)-piperidine (±)-3.-PPP. *Tetrahedron Asymm.* 1991, 2, 989–992). An X-ray structure determination of the salt formed from (–)-dibenzoyltartaric acid and 1 was used to determine the absolute stereochemistry of (–)-3 which is depicted in FIG. 1. As is apparent, the absolute stereochemistry of the (–)-isomer corresponds to that found in the WIN series of structures.

The optically pure (+)- and (–)-cis esters were converted to their respective alcohols (–)-5 and (+)-6 by lithium aluminum hydride reduction, and these alcohols were acylated with acetic anhydride in the presence of pyridine to give acetate derivatives (–)-7 and (+)-8. Compound 9, wherein $R^1$ is propyl, was prepared from alcohol 5 by oxidation to the aldehyde followed by Wittig reaction and catalytic hydrogenation. Compound 10 was prepared from the cis piperidine (–)-3 by hydrogenolysis over 10% palladium on charcoal in methanol at atmospheric pressure.

Figure 2:
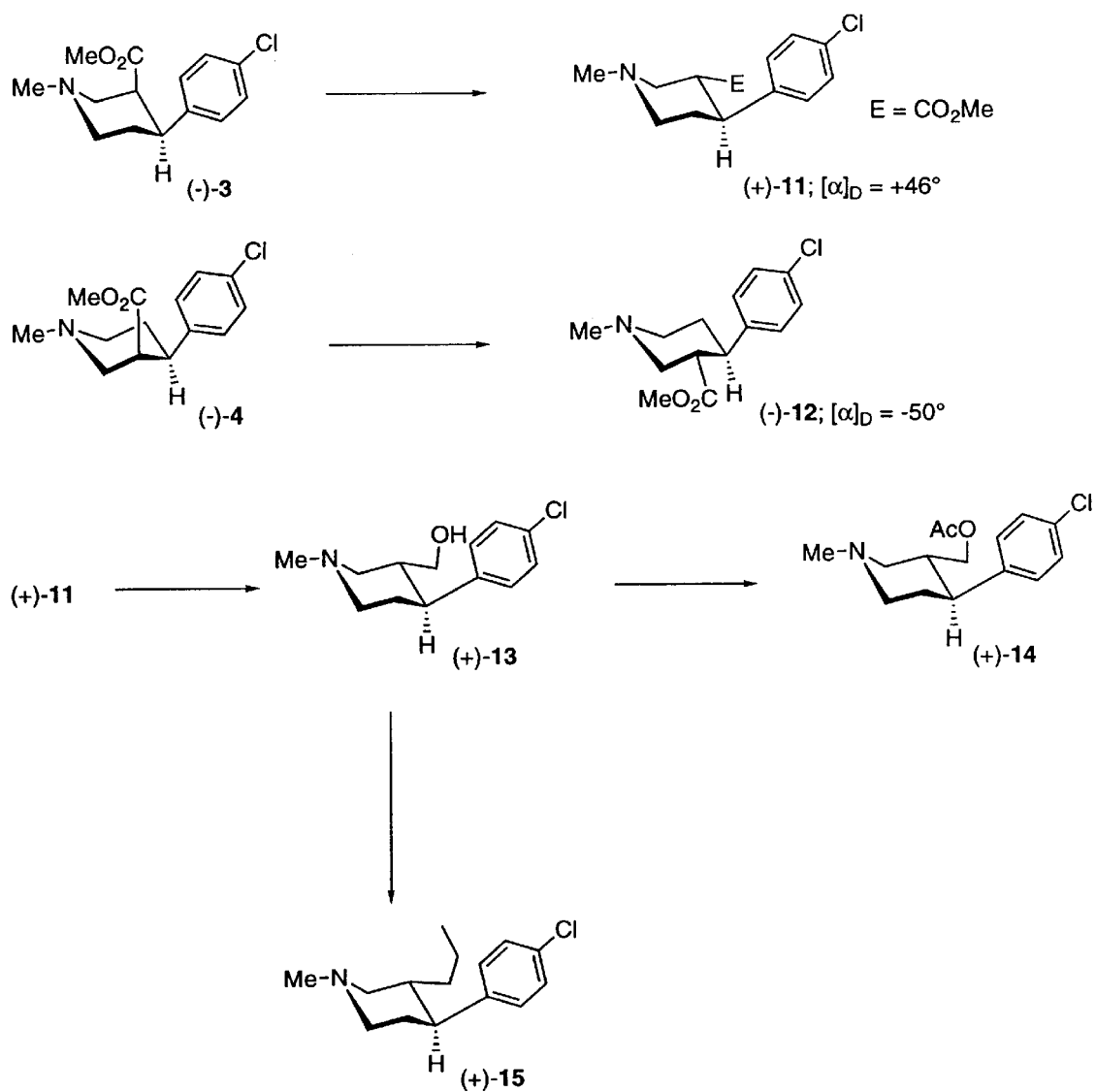

Because it was difficult to obtain satisfactory crystals from (±)-2 and dibenzoyltartaric acid, compounds (+)-11 and (–)-12 were prepared by the base-catalyzed epimerization of compounds (–)-3 and (–)-4 as shown in FIG. 2. The more active isomer (+)-11 was converted to the corresponding alcohol (+)-13 by reduction with lithium aluminum hydride in tetrahydrofuran. Acylation of alcohol (+)-13 with acetic anhydride and pyridine gave the acetate (+11-14. The n-propyl derivative (+)-15 was prepared by oxidation of alcohol (+)-13 followed by Grignard reaction using ethyltriphenyl-phosphonium bromide, and subsequent hydrogenation over 5% platinum on carbon.

Figure 3:
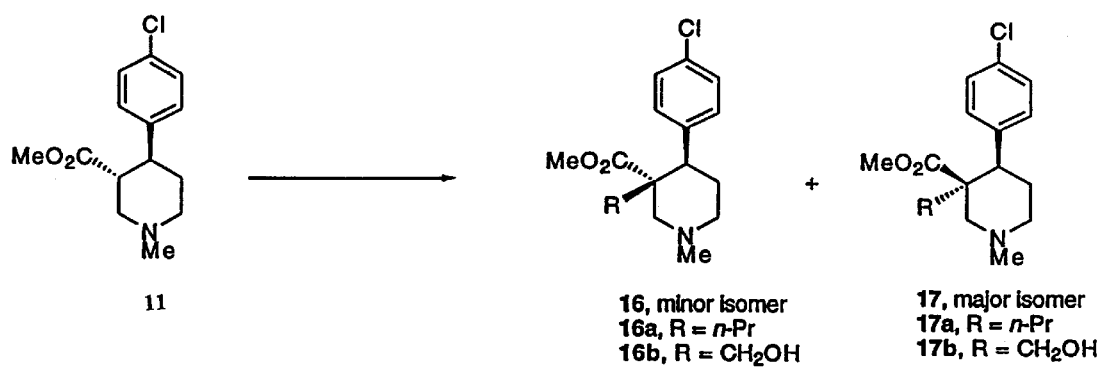

As illustrated in FIG. 3, a compound of formula I wherein is $R^2$ ($C_1$–$C_6$)alkyl and $R^1$ is —C(=O)$OR_a$ or cyano can be prepared from a corresponding compound of formula I wherein $R^2$ is hydrogen by deprotonation followed by alkylation.

Figure 4:
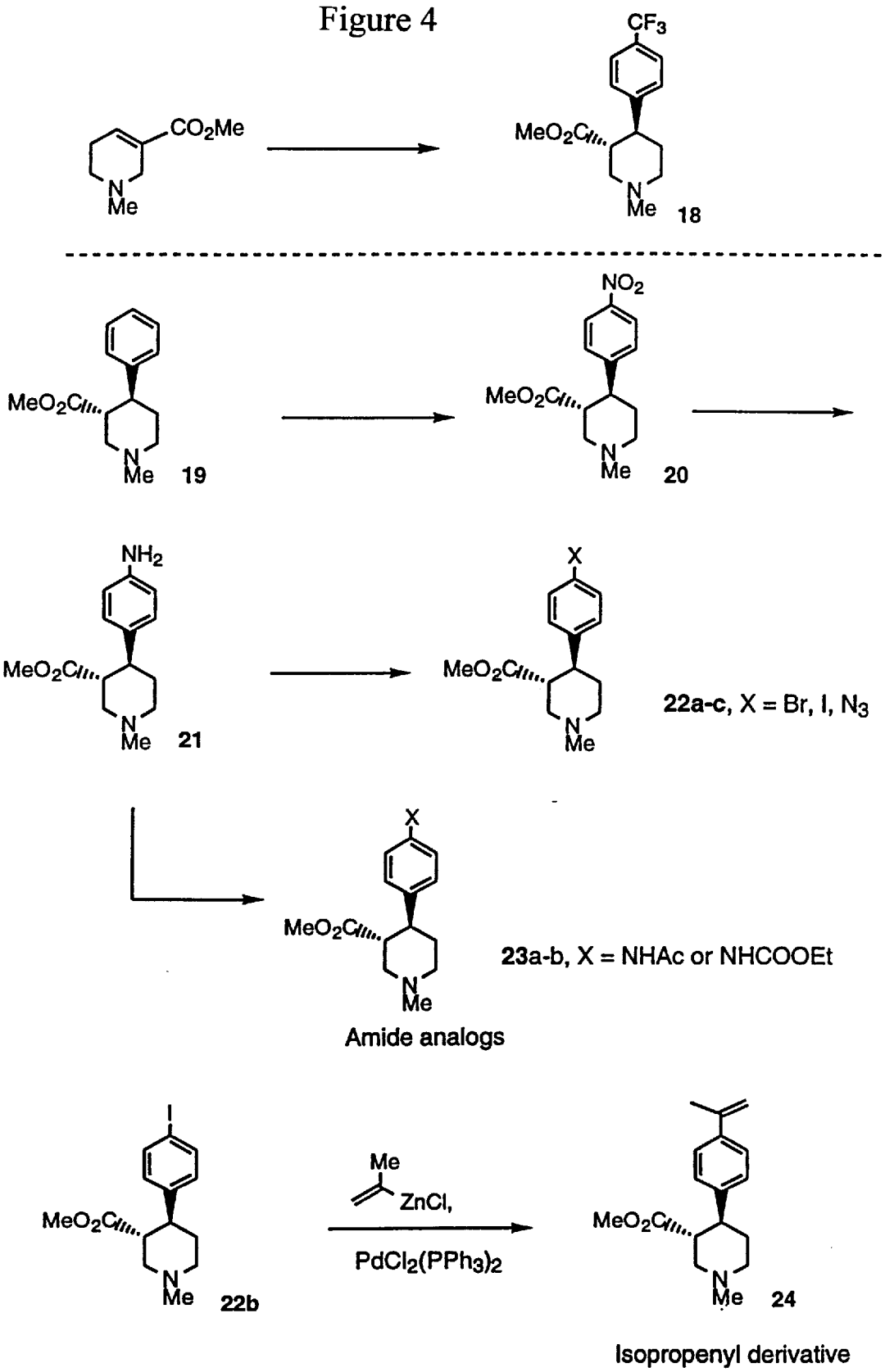

As illustrated in FIG. 4, compounds of formula I wherein $R_3$ is substituted phenyl can be prepared using procedures similar to those described in: Carroll, F. I., Gao, Y., Rahman, M. A., Abraham, P., Parham, K., Lewin, A. H., Boja, J. W., and Kuhar, M. J. (1991) Synthesis, ligand binding, QSAR and CoMFA study of 3b-(p-substituted phenyl)tropane-2 b-carboxylic acid methyl esters. *J. Med. Chem.*, 34, 2719–2725; or Blough, B. E., Abraham, P., Lewin, A. H., Kuhar, M. J., Boja, J. W., and Carroll, F. I. (1996) Synthesis and transporter binding properties of 3b-(4'-alkyl-, 4'-alkenyl-, and 4'-alkynylphenyl)nortropane-2b-carboxylic acid methyl esters: serotonin transporter selective analogs. *J. Med. Chem.*, 39, 4027–4035. Treatment of arecoline with 4-trifluoromethylphenyl magnesium bromide in ether followed by chromatographic separation of the resulting isomers gives compound 18. Nitration of compound 19 with nitronium tetrafluoroborate gives nitro compound 20, which can be reduced with Rany Ni to give amine 21. Treatment of amine 21 with HONO followed by copper(I) bromide, potassium iodide or sodium azide gives compounds 22a,c. Treatment of amine 21 with acetyl chloride or ethyl chloroformate gives amide 23a or carbamate 23b. Additionally, aryl iodide 22b can be treated with isopropenyl zinc chloride in the presence of a palladium catalyst bis (triphenylphosphine)palladium(II) chloride to yield isoprenyl compound 24.

Figure 5:
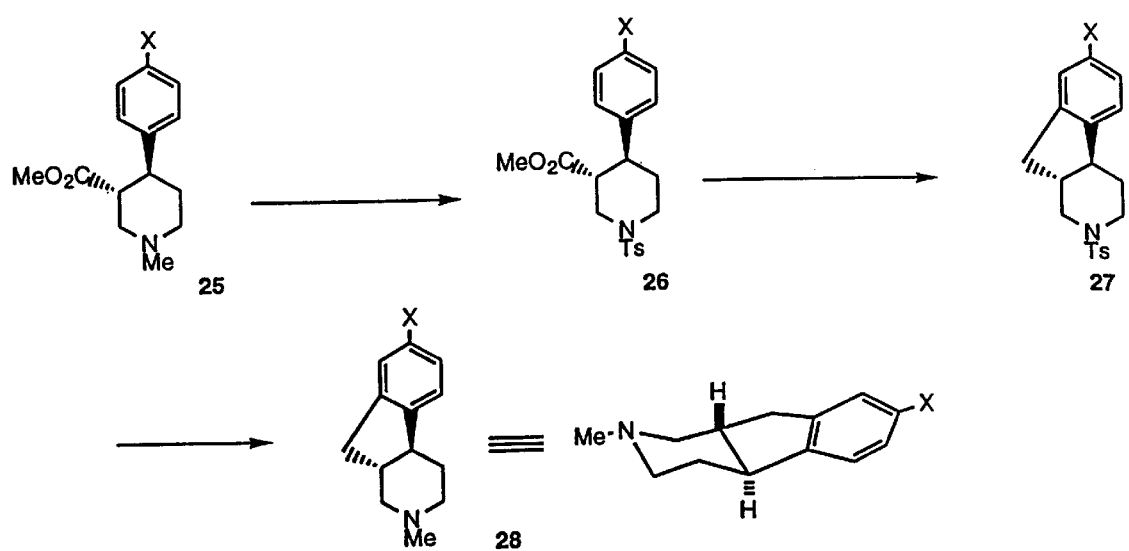

As shown in FIG. 5, compounds of formula I wherein $R^1$ is —$CH_2$—, or —$CH_2CH_2$—, wherein $R^1$ is also attached to a carbon at the ortho position of $R^3$; and $R^3$ is ($C_6$–$C_{10}$)aryl, or 5–10 membered heteroaryl can be prepared from a corresponding compound wherein $R^1$ is —C(=O)$OR_a$. Treatment of methyl amine 25 with 1-chloroethyl chloroform ate and methanol, followed by p-toluenesulfonyl chloride in pyridine gives the tosyl amine 26. Reduction of the ester with lithium aluminum hydride followed by treatment with $PBr_3$ and cyclization with $AlCl_3$ gives tricyclic compound 27 which can be deprotected by treatment with HBr/HOAc, and converted to the methyl amine 28 by reatment with with sodium hydroxide and formaldehyde, followed by reduction with sodium cyanoborohydride.

Figure 6:
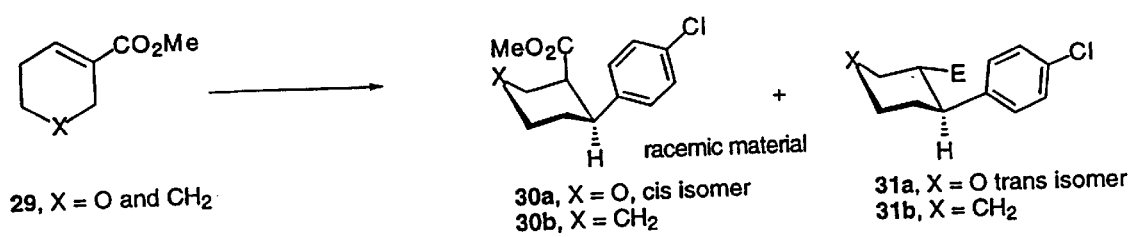

As illustrated in FIG. 6, compounds of formula I wherein Y is —$CH_2$— or —O— may be prepared from the appropriate dihydropyran-3-carboxylate or cyclohexenecarboxylate using procedures similar to those described above for the preparation of the corresponding compounds wherein Y is $NR_6$.

Figure 7:
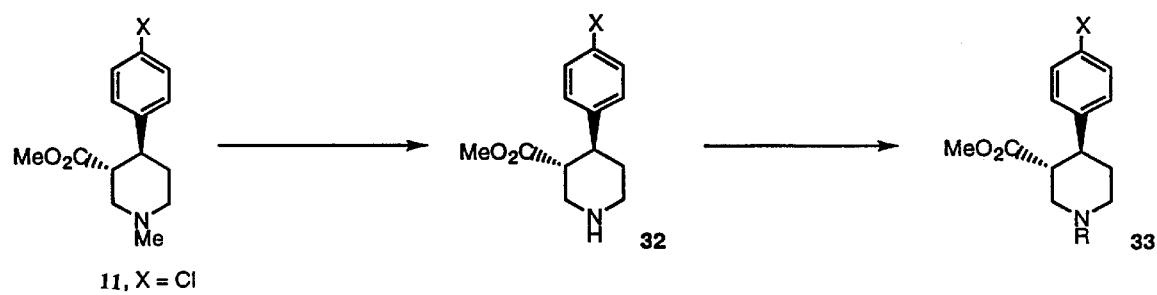

As illustrated in FIG. 7, a compound of formula I wherein $R^6$ is ($C_1$–$C_6$)alkyl or ($C_1$–$C_6$)alkanoyl (33) can be prepared from a corresponding compound of formula I wherein $R^6$ is methyl by treatment with ACEC1 in refluxing methanol to give amine 32, followed by alkylation or acylation of the amine using standard conditions.

Figure 8:
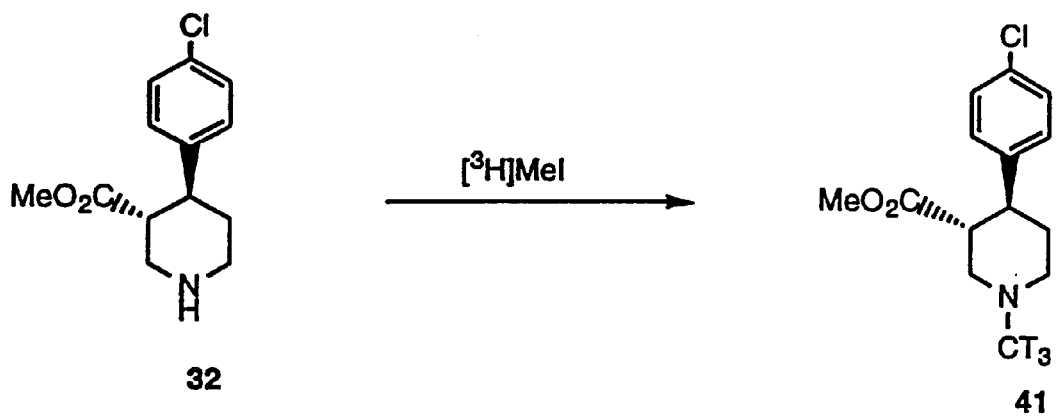

As shown in FIG. 8, a radiolabeled compound of formula I can be prepared by alkylation of an amine of formula 32 with a radiolabeled compound (e.g. IC[$^3$H]).

Figure 9:
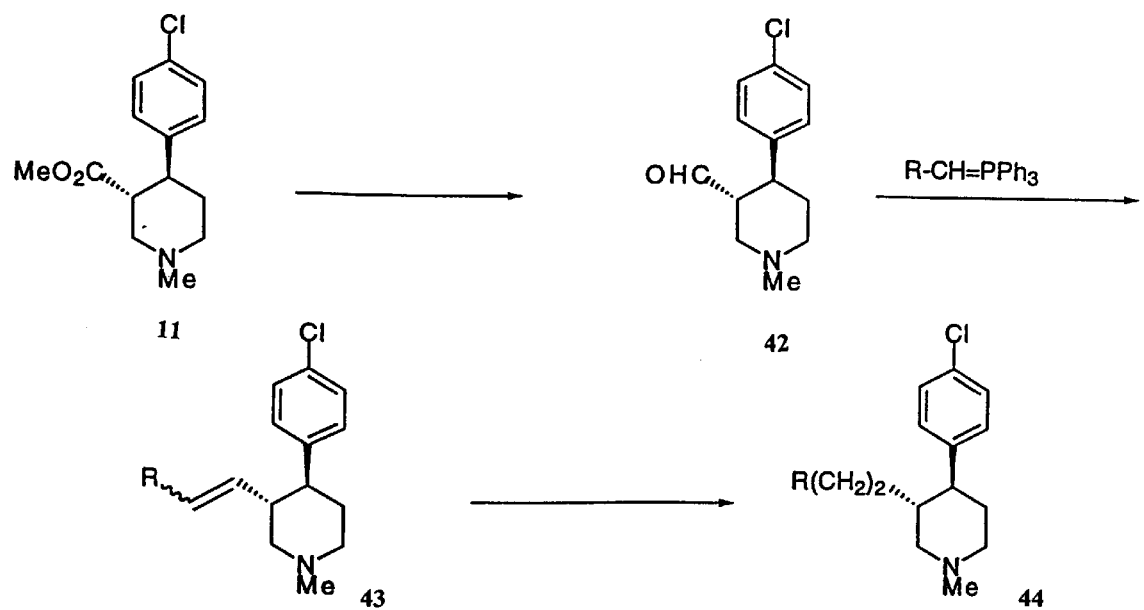

As shown in FIG. 9, compounds of formula I wherein $R^1$ is ($C_1$–$C_6$)alkyl, ($C_2$–$C_6$)alkenyl, or ($C_2$–$C_6$)alkynyl can be prepared using procedures similar to those described in Kozikowski, A. P., Saiah, M. K. E., Johnson, K. M., and Bergmann, J. S. (1995) Chemistry and biology of the 2b-alkyl-3b-phenyl analogues of cocaine: subnanomolar affinity ligands that suggest a new p harmacophore model at the C-2 position. *J. Med. Chem.*, 38, 3086–3093. Reduction of ester 11 with DIBAL followed by oxidation gives aldehyde 42. Treatment of compound 42 with a Grignard reagent gives an alkene of formula 43, which can be reduced with hydrogen over platinum on carbon to give an alkane of formula 44.

Figure 10:
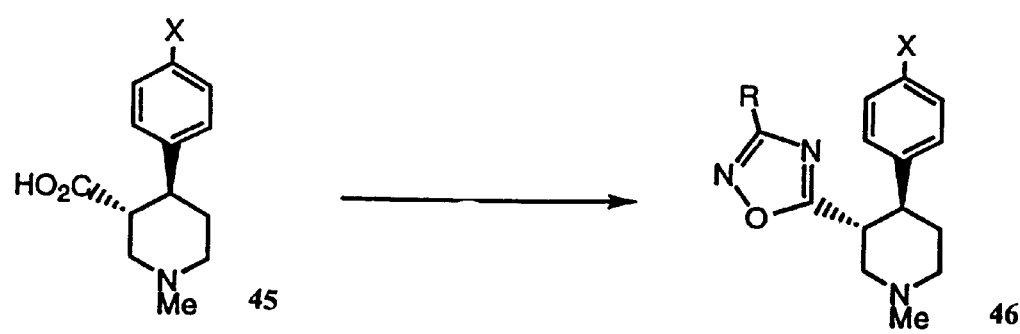

As illustrated in FIG. 10, a compound of formula I wherein $R^1$ is oxadiazolyl can be prepared by conversion of the ester group in a compound of formula I wherein $R^1$ is —C(=O)$OR_a$ to an acid, followed by acid chloride formation, and reaction with the appropriate amide oxime as described in: Kotian, P., Mascarella, S. W., Abraham, P., Lewin, A. H., Boja, J. W., Kuhar, M. J., and Carroll, F. I. (1996) Synthesis, ligand binding, and quantitative structure-activity relationship study of 3b-(4'-substituted phenyl)-2b-heterocyclic tropanes: evidence for an electrostatic interaction at the 2b-position. *J. Med. Chem.* 39, 2753–2763.

It is noted that many of the starting materials employed in the synthetic methods described above are commercially available or are reported in the scientific literature, and that certain compounds of formula I are useful as intermediates to prepare other compounds of formula I.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable acid addition salts of inorganic acids may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable, solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%. Single dosages for injection, infusion or ingestion will generally vary between 50–1500 mg, and may be administered, i.e., 1–3 times daily, to yield levels of about 0.5–50 mg/kg, for adults.

Compounds of the invention may also be used as imaging agents when labeled with a radionuclide. As illustrated in FIG. 9, the radionuclide (such as tritium, iodine-125, iodine-131, iodine-123, astatine-210, carbon-11, carbon-14, nitrogen-13, fluorine-18) may be incorporated into, or attached directly to the core structure, as by halogenation; or the radionuclide (such as Tc-99m, Re-186) may be attached to a linking group or bound by a chelating group which is then attached to the compound of formula I directly, or by means of a linker. Radiolabeling techniques such as these are routinely used in radiopharmaceutical chemistry.

Radiolabeled compounds of the invention are generally useful as imaging agents to diagnose neurological disease (e.g. a neurodegenerative disease) or a mental condition or to follow the progression or treatment of such a disease or condition in a mammal (e.g. a human). The radiolabeled compounds of the invention and can conveniently be used in conjunction with imaging techniques such positron emission tomography (PET) or single photon emission computerized tomography (SPECT).

The pharmacological activity of compounds of the invention can be demonstrated using standard pharmacological models which are known in the art, or can be demonstrated using the models that are described or cited hereinbelow.

Representative compounds of the invention 1–15 were tested for their ability to displace [$^3$H]WIN-35428 binding from rat striatal membranes and to inhibit the high-affinity uptake of [$^3$H]dopamine into rat striatal nerve endings (synaptosomes) in accordance with protocols previously described by Boja et al. *Mol Pharmacol.* 1991, 39, 339. The results of these assays are provided in Table 1.

TABLE 1

IC$_{50}$ Values for Compounds of Formula I in [$^3$H]WIN 35,428 Binding and in the Inhibition of [$^3$H]Dopamine Uptake

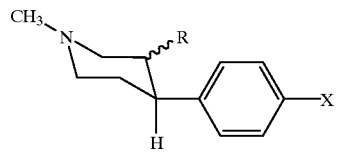

| Compound number | R | X | IC$_{50}$ (nM) [$^3$H]WIN 35,428 binding | IC$_{50}$ (nM) [$^3$H]dopamine uptake |
|---|---|---|---|---|
| cocaine | — | — | 101.6 ± 9.4 | 239.1 ± 1.1 |
| (±)-1 | β-CO$_2$Me | Cl | 53.7 ± 1.9 | 37.8 ± 7.9 |
| (±)-2 | α-CO$_2$Me | Cl | 196.8 ± 7.9 | — |
| (−)-3 | β-CO$_2$Me | Cl | 24.8 ± 1.6 | 85.23 ± 2.6 |
| (+)-4 | β-CO$_2$Me | Cl | 1362 ± 125 | 5092 ± 172 |
| (−)-5 | β-CH$_2$OH | Cl | 75.3 ± 6.2 | 49.0 ± 3.0 |
| (+)-6 | β-CH$_2$OH | Cl | 442 ± 32 | — |
| (−)-7 | β-CH$_2$OAc | Cl | 44.7 ± 10.5 | 62.9 ± 2.7 |
| (+)-8 | β-CH$_2$OAc | Cl | 928 ± 43 | 2027 ± 82 |
| (−)-9 | β-nPr | Cl | 3.0 ± 0.5 | 8.3 ± 0.6 |
| (−)-10 | β-CO$_2$Me | H | 769 ± 19 | — |
| (+)-11 | α-CO$_2$Me | Cl | 57.3 ± 8.1 | 34.6 ± 3.2 |
| (−)-12 | α-CO$_2$Me | Cl | 653 ± 38 | 195 ± 8 |
| (+)-13 | α-CH$_2$OH | Cl | 240 ± 18 | 683 ± 47 |
| (+)-14 | α-CH$_2$OAc | Cl | 461 ± 11 | — |
| (+)-15 | α-nPr | Cl | 17.2 ± 0.5 | 23.2 ± 2.2 |

Analog Binding at Neurotransmitters.

Determination of inhibitory binding potencies of analogues at dopamine, serotonin, and norepinephrine transporters can be carried out using standard receptor binding assays which are known in the art.

A. Dopamine Transporter Binding

Dopamine transporters can be assayed using the method described by Boja, J. W., Rahman, M. A., Philip, A., Lewin, A. H., Carroll, F. I. and Kuhar, M. J. (1991) Isothiocyanate derivatives of cocaine: Irreversible of ligand binding at the dopamine transporter. *Mol Pharmacol.*, 39, 339.

B. Serotonin Transporter Binding

Inhibition of [$^3$H]binding to the serotonin transporter can be assayed according to previously published methods: Boja, J. W., Rahman, M. A., Philip, A., Lewin, A. H., Carroll, F. I. and Kuhar, M. J. (1991) Isothiocyanate derivatives of cocaine: Irreversible of ligand binding at the dopamine transporter. *Mol. Pharmacol.*, 39, 339.

C. Norepinephrine Transporter Binding

Binding to the norepinephrine transporter can be assayed using a method described by Carroll, F. I., Grey, J., Abraham, P., Kuzemnko, M .A., Lewin, A. H., Boja, J. W., and Kuhar, M. J. (1993) 3-Aryl-2-(3'-substituted-1',2',4'-oxadiazole-5'-yl)tropane analogues of cocaine: Affinities at the cocaine binding site at the dopamine, serotonin, and norepinephrine transporters. *J. Med Chem.*, 36, 2886–2890.

Uptake Studies

A. [$^3$H]Dopamine Uptake Studies

Inhibition of [$^3$H]dopamine uptake can be determined using the method of Boja, J. W., McNeil, R. M., Lewin, A. H., Abraham, El., Carroll, F. I., and Kuhar, M. J. (1992) Selective dopamine transporter inhibition by cocaine analogs. *Neuroreport*, 3, 984.

B. [$^3$H]Serotonin Uptake Studies

Inhibition of [$^3$H]serotonin uptake can be determined in fresh rat hind brain tissue. The assay can be conducted as described above, with some modifications. The final tissue concentration will be approximately 2 mg/mL, and the final [$^3$H]serotonin concentration will be 5.0 nM. Non-specific uptake of [$^3$H]serotonin can be defined using 1 μM citalopram.

C. [$^3$H]Norepinephrine Uptake Studies

Inhibition of [$^3$H]norepinephrine uptake can be determined in fresh rat cortex. The assay can be conducted in a manner similar to that described for [$^3$H]dopamine uptake studies, with some modifications. The final tissue concentration will be approximately 10 mg/mL, and the final [$^3$H]norepinephrine concentration will be 5.0 nM. The non-specific uptake of [$^3$H]norepinephrine can be defined using 1 μM desipramine.

Intravenous Safety

Cocaine and a number of other tropane analogs are potent inhibitors of norepinephrine re-uptake and possess local anesthetic actions. These properties may indicate significant potential for cardiovascular and central nervous system toxicity.

The test compounds with 10 μM or greater affinity for the dopamine transporter can be tested in rats for intravenous safety according to the previously published procedure. Tella, S. R., Korupolu, G. R., Schindler, C. W., and Goldberg, S. R. (1992) Pathophysiological and pharmacological mechanisms of acute cocaine toxicity in conscious rats. *J. Pharmacol. Exp. Ther.*, 262, 936–946.

Behavioral Testing

A. Locomotor activity

The locomotor effects of compound 2 were evaluated using male Swiss Webster mice according to previously published procedures: Izenwasser, S., Terry, P., Heller, B., Witkin, J. M., and Katz, J. L. (1994) Differential relationships among dopamine transporter affinities and stimulant potencies of various uptake inhibitors. *Eur. J. Pharmacol.*, 263, 277–283.

Cocaine (10 mg/kg, i.p.) produced a significant (P<0.05) increase in the distance traveled and stereotypic behavior as compared to saline control responses in Sprague-Dawley rats. In contrast to cocaine, piperidine analog 2 (3–20 mg/kg i.p.) did not alter the distance traveled. However, piperidine 2 at 10 and 20 mg/kg doses produced a small, statistically nonsignificant increase in stereotypic time. The time-course data indicate that this small increase in stereotypic behavior is persistent at 90 minutes following the drug injection, while the stereotypic response to cocaine showed a clear tendency to decline at this time period. Thus the small behavioral responses to the piperidine analog appear to last longer than that of cocaine. The motor effects of higher doses of the piperidine analog were not tested as these doses produce convulsions.

B. Drug-discrimination

Compound 2 was evaluated in the drug discrimination procedure described by: Callahan, P. M., Bryan, S. K., and Cunningham, K. A. (1995) Discriminative stimulus effects of cocaine: antagonism by dopamine DI receptor blockade in the amygdala. *Pharmacol. Biochem. Behav.*, 51, 759–766.

In Substitution tests, amphetamine administration engendered a dose-dependent and complete substitution for the discriminative stimulus effects of amphetamine, whereas administration of the piperidine analog 2 resulted in a maximum of 53% amphetamine-lever responding. Response rates remained fairly stable across all test doses of amphetamine and piperidine analog 2.

Cocaine (1.25–10 mg/kg) administration resulted in a dose-related increase in cocaine-appropriate responding, whereas piperidine analog 2 (5 and 20 mg/kg) engendered a maximum of 40% cocaine-lever responding. Response rates following piperidine analog 2 (5 and 10 mg/kg) were substantially lower than those observed following cocaine (10 mg/kg) administration. Co-administration of piperidine analog 2 (10 mg/kg) plus cocaine (1.25 and 5 mg/kg) did not significantly alter drug choice [$F(1,7)=1.35$, $p=0.28$] or response rate performance [$F(1,7)=4.84$, $p=0.06$] from that observed following administration of 1.25 and 5 mg/kg of cocaine alone (data not shown). This result is in contrast to other dopamine uptake inhibitors that are known to cause a leftward shift in cocaine's dose-response function. These results suggest that the piperidine analog differs from other uptake inhibitors in lacking the potentiation of cocaine's discriminative stimulus effects.

C. Intravenous drug self-administration

Compounds 2 and 3 were evaluated using the intravenous drug self-administration procedures described by: Tella, S. R., Ladenheim, B., Andrews, A. M., Goldberg, S. R., and Cadet, J. L. (1996) Differential reinforcing effects of cocaine and GBR-12909: Biochemical evidence for divergent neuroadaptive changes in the mesolimbic dopaminergic system. *J. Neurosci.*, 16, 7416–7427.

Rats were initially trained to lever press for food pellets in standard operant boxes. Following lever press training, rats were implanted with polyvinyl chloride catheters into femoral veins under halothane anesthesia (2–3% in medical grade oxygen) and were allowed to recover for an additional 7 days before initiation of i.v. drug self-administration testing. During drug self-administration sessions, food pellets were no longer delivered, and instead intravenous injections of drugs were delivered by way of the catheter. Each completion of 10 lever press responses (FR10) resulted in an i.v. infusion of cocaine (1 mg/kg/infusion) delivered over a 1 second period.

Following approximately 3 weeks of cocaine self-administration, the extinction test was done by substituting saline (0.25 ml/kg) for cocaine for 5 days. Following extinction, re-acquisition of cocaine (1 mg/kg/infusion) self-administration was tested for 5 days. Following re-acquisition of cocaine self-administration, the saline extinction test was repeated. Following this second extinction test, self-administration of piperidine analog 2 was studied at doses of 1, 3, and 0.3 mg/kg/infusion in that order. Each dose was tested for five days. During all the re-acquisition test days, a priming infusion was given at the start of the session on each day.

Cocaine maintained significantly ($P<0.05$) higher rates of responding as compared to the responding during the saline extinction test. The substitution of saline for cocaine led to a decline in the response rate. The substitution of piperidine analog 2 (0.3–3 mg/kg/infusion) for saline failed to restore the self-administration responding. The number of infusions of the piperidine analog delivered at all of the doses tested were not significantly different from that of the saline extinction test. These data suggest that the piperidine analog, unlike cocaine, lacks positive reinforcing effects. In contrast, the piperidine analog 3 is cocaine-like in this test, as evidenced by the fact that rats reliably self-administered this compound (0.125–0.5 mg/kg infusion).

D. Effects of test compounds on cocaine self-administration and food reinforcement The effect of pretreatment with test compound on cocaine self-administration can be studied. Five minutes following intravenous injection of test compounds, rats can be tested for cocaine self-administration. The doses that fall on both the ascending and the descending portions of the cocaine dose-response function can be tested following pretreatment with test compounds. This allows for a determination of whether there is a left- or rightward shift or downward shift in the cocaine dose-response function. Compounds showing overall reduction (downward shift) in cocaine self-administration can be further tested for the specificity of this effect. This can be done by studying the effect of test compound on non-drug reinforcers such as food.

PET Evaluation

The cis and trans isomers of 4-(4-chlorophenyl)-3-(carbomethoxy)piperidine were labeled via N-methylation. $^{11}$C-methyl iodide was bubbled into a solution of each of the piperidine isomers (1.5 mg free base in 0.3 cc DMSO) and the mixtures were heated at 110° C. for 7 minutes. The products were purified by HPLC on a C-18 cartridge eluted with MeOH: phosphate/triethylamine buffer, pH 7.2 (60:40). The $^{11}$C-labeled drugs were produced in good radiochemical yield [~15%@EOS]. Radiochemical purities of the final products were>98% and specific activity were routinely>2,000 mCi/$\mu$mole [EOS].

After passage through a 0.22 $\mu$m filter, the sterile products were administered to three Rhesus monkeys and dynamic PET images were acquired over 90 minutes. Both isomers accumulated rapidly in the striatum with the cis isomer exhibiting greater nonspecific accumulation in the cortex. Studies with low specific activity tracer showed reduced striatal-to-cerebellar ratios compared with high specific activity preparations. When unlabeled CFT was administered 60 minutes after injection of the trans isomers, a selective decrease in the striatal activity was observed; consistent with in vivo binding to the dopamine transporter.

These results establish that both the cis- and trans isomers of 4-(4-chlorophenyl)-3-carbomethoxy-N-methylpiperidine have high levels of specific binding to striatal dopamine transporter sites.

The 3-n-propyl derivative (–)-9 was found to have a binding affinity of 3 nM. Thus compound 9 is 33-fold more potent than cocaine in binding affinity, and 29-fold more potent in its inhibition of dopamine uptake. The above results demonstrate that representative compounds of formula I possess significant binding activity at the dopamine receptor. Accordingly compounds of the invention may be useful as therapeutic agents for the treatment of drug abuse (e.g. cocain addiction). Additionally, compounds of formula I, and in particular, compounds wherein $R^6$ is hydrogen, may also possess activity as serotonin reuptake inhibitors. Accordingly, compounds of formula I may also be useful for inhibiting serotonin reuptake, and thus for treating Parkinson's disease or depression.

The invention will now be illustrated by the following non-limiting examples, wherein unless otherwise stated: starting materials were obtained from Aldrich Chemicals or from other commercial suppliers; diethyl ether and cyclohexane were distilled from phosphorus pentoxide; tetrahydrofuran was freshly distilled under nitrogen from sodium-benzophenone; infrared ("IR") spectra were recorded on an ATI Mattson Genesis spectrometer; proton $^1H$ and carbon $^{13}C$ nuclear magnetic resonance ("NMR") spectra were obtained with a Varian Unity Inova instrument at 300 and 75.46 MHz; $^1H$ chemical shifts ($\delta$) are reported in ppm downfield from internal TMS; $^{13}C$ chemical shifts are referred to $CDCl_3$ (central peak, $\delta$=77.0 ppm), benzene-$d_6$ (central peak, $\delta$=128.0 ppm), or DMSO-$d_6$ (central peak, $\delta$=39.7 ppm); when appropriate NMR assignments were made with the help of COSY, DEPT, and HETCOR experiments; melting points were determined in Pyrex capillaries with a Thomas Hoover Unimelt apparatus and are uncorrected; mass spectra were measured in the EI mode at an ionization potential of 70 eV; thin layer chromatography ("TLC") was performed on Merck silica gel 60$F_{254}$ glass plates; column chromatography was performed using Merck silica gel (60–200 mesh); each of compounds 1–15 gave satisfactory combustion analysis; and the following abbreviations are used: DMSO=dimethyl sulfoxide; ether=diethyl ether; THF=tetrahydrofuran; and DCM=dichloromethane.

EXAMPLES

Example 1

(±)-cis-Methyl 4-(4-Chlorophenyl)-1-methylpiperidine-3-carboxylate (1).

To a solution of 4-chlorophenylmagnesium bromide (166 mL, 1.0 M in ether) in ether (700 mL) was added dropwise at –10° C. a solution of arecoline free base (12.9 g, 83 mmol, obtained from the hydrobromide by treatment with sodium bicarbonate and extraction into methylene chloride) in ether (300 mL). The mixture was stirred at –10° C. for 30 minutes, then poured onto crushed ice and treated slowly with 10% HCl (200 mL). The aqueous layer was separated, washed with ether (200 mL), and treated, while cooling in an ice bath, with a saturated solution of sodium bicarbonate (100 mL). The mixture was extracted with ether (2×200 mL), and the combined organic phases were washed with brine (200 mL), dried, and concentrated under reduced pressure. The crude mixture was crystallized from EtOAc/hexane to afford the the title compound 1 (5.0 g, 22%) as a white solid. Concentration of the mother liquor gave a mixture of compounds 1 and 2 that was separated by flash chromatography on silica gel using ether/$Et_3N$ 9/1 as eluent to give additional title compound (total 12.4 g, 56%): mp 98–99° C.; $^1H$ NMR ($CDCl_3$) $\delta$1.74–1.86 (m, $H_{5eq}$), 2.07 (dt, $H_{6ax}$, J=3.0 and 11.4 Hz), 2.28 (s, 3H), 2.35 (dd, $H_{2'}$, J=3.6 and 11.7 Hz), 2.66 (dq, $H_{5ax}$, J=3.9 and 12.0 Hz), 2.78 (dt, $H_4$, J=3.6 and 12.0 Hz), 2.9–3.06 (m, $H_3$ and $H_{6eq}$), 3.18 (bd, $H_{2''}$, J=12.0 Hz), 3.52 (s, 3H), 6.2–6.35 (m, 4H); $^{13}C$ NMR ($CDCl_3$) $\delta$26.42 ($C_5$), 41.27 ($C_4$), 46.06 ($C_3$), 46.53 ($C_7$), 51.25 ($C_9$), 55.88 ($C_6$), 58.36 ($C_2$), 128.08 ($C_{11}$, $C_{15}$), 128.95 ($C_{12}$, $C_{14}$), 131.79 ($C_{13}$), 141.54 ($C_{10}$), 172.47 ($C_8$); MS m/z (%) 267 ($M^+$, 7), 208 (14), 128 (6), 70 (29), 44 (100).

Compound 1 was dissolved in a methanolic solution of hydrochloric acid gas and the resulting solid was triturated with ether to give compound 1 • HCl: $^1H$ NMR (methanol-$d_4$) $\delta$ 2.05 (bd, 1H, J=4.0 Hz), 2.53 (bq, 1H, J=10.8 Hz), 2.94 (s, 3H), 3.14–3.5 (m, 4H), 3.45 (s, 3H), 3.6–3.7 (m, 1H), 3.78 (d, 1H, J=12.9 Hz), 7.22 (d, 2H, J=8.4 Hz), 7.35 (d, 2H, J=8.4 Hz).

Example 2

(±)-cis-Methyl 4-(4-Chlorophenyl)-1-methylpiperidine-3-carboxylate (2).

Concentration of the mother liquor from Example 1 gave a mixture of compounds 1 and 2. Flash chromatography on silica gel using ether/$Et_3N$ 9/1 as eluent gave compound 2 (2.0 g, 18%): $^1H$ NMR (benzene-$d_6$) $\delta$ 1.4–1.5 (m, 1H), 1.62 (dq, 1H, J=3.9 and 12.6 Hz), 1.75 (dt, 1H, J=2.7 and 12.0 Hz), 2.06 (s, 3H), 2.0–2.15 (m, 1H), 2.54–2.63 (m, 1H), 2.68 (dt, 1H, J=4.2 and 11.7 Hz), 2.86–3.0 (m, 2H), 3.08 (s, 3H), 6.87 (d, 2H, J=8.7 Hz), 7.07 (d, 2H, J=8.7 Hz); $^{13}C$ NMR ($CDCl_3$) $\delta$33.1, 44.0, 46.1, 49.1, 51.5, 55.7, 58.1, 128.6, 128.7, 132.3, 141.9, 173.4; MS m/z (%) 267 ($M^+$, 17), 208 (30), 128 (16), 114 (16), 43 (100).

Using a procedure similar to that described in Example 1, the hydrochloride salt of compound 2 was prepared: compound 2 • HCl: $^1H$ NMR (methanol-$d_4$) $\delta$2.04–2.16 (m, 2H), 2.97 (s, 3H), 3.0–3.3 (m, 4H), 3.47 (s, 3H), 3.56–3.66 (m, 1H), 3.7–3.8 (m, 1H), 7.25 (d, 2H, J=8.4 Hz), 7.34 (d, 2H, J=8.4 Hz).

Example 3

(−)-Methyl 4β-(4-chlorophenyl)-1-methylpiperidine-3β-carboxylate (3).

To a solution of compound 1 (6.4 g, 24 mmol) in MeOH (200 mL) was added a solution of dibenzoyl-L-tartaric acid (8.9 g, 24 mmol) in MeOH (100 mL). The resulting mixture was stirred at room temperature for 5 hours, filtered, and the white precipitate washed with MeOH (20 mL). This tartrate salt was treated with a saturated solution of $NaHCO_3$ (150 mL) and the mixture extracted with $CHCl_3$ (3×100 mL). The combined organic phases were washed with brine (150 mL), dried, and concentrated under reduced pressure to afford the title compound (2.0 g) as a white solid: mp 98–99° C.; $[\alpha]^{25}_D$ –56° (c 1.0, EtOH).

Using a procedure similar to that described in Example 1, the hydrochloride salt of compound 3 was prepared: compound 3 • HCl; $[\alpha]^{25}_D$ –130° (c 1.0, EtOH).

Single Crystal X-Ray Analysis was preformed on the (−)-Dibenzoyltartrate of (3) as described below. A clear rectangular 0.06×0.08×0.52 mm crystal, $C_{14}H_{19}O_2ClN^+$ $C_{18}H_{13}O_8^−$, FW=626.04, was selected for data collection. Data were collected on a computer controlled Siemens CCD 1K area detector system with a Siemens PLATFORM goniometer using a Rigaku rotating anode source and Gobel mirrors (Cu K$\alpha$ radiation, $\lambda$=1.54178 Å, T=295 K). Data collection nominally covered a hemisphere in reciprocal space by combining six sets of exposures with different 2$\theta$ and $\phi$ angles: each exposure covered a range of 0.75° in $\omega$. The crystal to detector distance was 5.09 cm, and coverage of a unique set was 98% complete to 1.0 Å resolution. The crystal decay was monitored by repeating 50 of the initial frames at the end of data collection and was found to be 2.7%. A least-squares refinement using 176 centered reflections within 16.2<2$\theta$<34.4° gave the orthorhombic $P2_12_12_1$ cell, a=7.752(3), b=14.691(5) c=27.502(8) Å, with V=3132.2 (17) Å$^3$, Z=4, and $d_{calc}$=1.328 gm/cm. A total of 8342 reflections were to 2$\theta_{-max}$=100°, of which there were 2923 independent reflections. Corrections were applied for Lorentz and polarization effects. An empirical absorption correction was applied using equivalent reflections (SADABS), $\mu$=1.577 mm$^{-1}$. Max. and min. transmission were 0.44 and 0.88, respectively. The structure was solved by direct methods with the aid of the program SHELXT1 and refined on F$^2$ with full matrix least-squares. The 398 parameters refined include the coordinates and anisotropic thermal parameters for all non-hydrogen atoms. Hydrogens were included using a riding model. The final R values for the 2244 observed reflections with $F_o$>4$\sigma$(|$F_o$|) were R=0.086 and wR(F$^2$)=0.208. The goodness of fit parameter was 1.07, and final difference Fourier excursions were 0.41 and −0.27 eÅ$^{-3}$. The absolute configuration determination was based on a method suggested by D. Rogers. The absolute structure parameter which should be near 0.0 for the correct choice of chirality and 1.0 for an incorrect choice was 0.04(6). The compound also contained a chiral anion, (−)-dibenzoyltartaric acid.

Example 4

(+)-Methyl 4β-(4-Chlorophenyl)-1-methylpiperidine-3β-carboxylate (4).

To the mixture of enantiomers derived from the mother liquor of Example 3 (4.2 g, 15.7 mmol) in MeOH (150 mL) was added a solution of dibenzoyl-D-tartaric acid (5.8 g, 15.7 mmol) in MeOH (50 mL). The resulting mixture was stirred at oom temperature 5 hours, filtered, and the white precipitate was washed with MeOH (10 mL). This tartrate salt was treated with a saturated solution of NaHCO$_3$ (100 mL) and the mixture extracted with CHCl$_3$ (3×70 mL). The combined organic phases were washed with brine (150 mL), dried, and concentrated under reduced pressure to afford the title compound (2.2 g) as a white solid: mp 98-99 IC; [α]$^{25}_D$ +56° (c 1.0, EtOH).

The hydrochloride salt was prepared by dissolution of the free base of compound 4 in a methanolic solution of HCl(g), concentration, and final trituration of the crude salt with ether: [α]$^{25}_D$ +126° (c 1.0, EtOH). Example 5. (−)-4β-(4—Chlorophenyl)-3β-(hydroxymethyl)-1-methylpiperidine (5).

To a solution of 3 (1.0 g, 3.7 mmol) in THF (30 mL) was added portionwise LiAlH$_4$ (0.3 g, 7.5 mmol). The resulting mixture was stirred at room temperature for 2 hours. A saturated solution of Rochelle salt (30 mL) was added followed by extraction with EtOAc (100 mL). The organic phase was washed with brine (100 mL), dried, and concentrated under reduced pressure to afford the title compound (0.9 g, 98%) as a colorless oil: [α]$^{25}_D$ −70° (c 1.0, EtOH); $^1$H NMR (CDCl$_3$) a 1.64–1.84 (m, H$_3$ and H$_{5eq}$), 2.11 (dt, H$_{63}$, J=3.3 and 11.7 Hz), 2.29 (s, 3H), 2.45 (dt, H$_1$·, J=2.7 and 11.4 Hz), 2.55 (dq, H$_{5ax}$, J=4.2 and 12.6 Hz), 2.84 (dt, H$_4$, J=4.5 and 13.5 Hz), 3.0–3.1 (m, H$_{6eq}$), 3.14 (br d, H$_{2''}$, J=11.4 Hz), 3.54 (dt, H$_8$, J=2.4 and 10.8 Hz), 3.70 (dd, H$_8$, J=3.3 and 11.1 Hz), 7.24 (d, 2H, J=8.7 Hz), 7.29 (d, 2H, J=8.7 Hz); $^{13}$C NMR (CDCl$_3$) δ 27.9 (C$_4$), 40.2 (C$_2$), 43.5 (C$_3$), 46.3 (C$_6$), 56.2 (C$_1$), 61.4 (C$_5$), 64.5 (C$_8$), 128.4 (C$_{11}$, C$_{15}$), 129.2 (C$_{12}$, C$_{14}$), 131.9 (C$_{13}$), 142.1 (C$_{10}$); MS m/z (%) 239 (M$^+$, 6), 208 (6), 100 (16), 44 (100).

Example 6

(+)-4β-(4-Chlorophenyl)-3β-(hydroxymethyl)-1-methylpiperidine (6).

Using a procedure similar to that described in Example 5, except replacing the compound 3 used therein with compound 4, the title compound 6 was prepared (82%) as a colorless oil; [α]$^{25}_D$ +67° (c 1; EtOH).

Example 7

(−)-3β-(Acetoxymethyl)-4β-(4-chlorophenyl)-1-me(thylpiperidine (7).

To a solution of compound 5 (90 mg, 0.38 mmol) in pyridine (2 mL) was added acetic anhydride (0.5 mL). The resulting solution was stirred at room temperature for 15 hours, concentrated under reduced pressure, diluted with EtOAc (30 mL), and washed with a saturated solution of NH$_4$Cl (2×20 mL). The organic solution was dried and concentrated under reduced pressure to afford the title compound (0.10 g, 95%) as a white solid: mp 76° C.; [α]$^{25}_D$ −109° (c 0.75; EtOH); R$_f$ 0.6 (ether/Et$_3$N 9.5/0.5); $^1$H NMR (benzene-d$_6$) δ1.21 (br d, 1H, J=11.4 Hz), 1.52 (s, 3H), 1.72 (dq, 1H, J=3.0 and 12.3 Hz), 1.6–1.7 (m, 1H), 1.86 (dd, 1H, J=2.7 and 11.4 Hz), 2.0–2.1 (m, 1H), 2.09 (s, 3H), 2.40 (dt, 1H, J=3.9 and 11.4 Hz), 2.67 (br d, 1H, J=8.1 Hz), 2.91 (d, 1H, J=11.4 Hz), 3.90 (dd, 1H, J=4.5 and 10.8 Hz), 4.47 (dd, 1H, J=9.6 and 10.5 Hz), 6.68 (d, 2H, J=8.4 Hz), 7.09 (d, 2H, J=8.4 Hz); $^{13}$C NMR (CDCl$_3$) δ20.8, 25.6, 39.6, 41.9, 46.5, 56.2, 57.8. 62.5, 128.4, 128.5, 132.0, 141.5, 170.9; MS m/z (%) 281 (M$^+$, 6), 238 (6), 208 (15), 142 (7), 44 (100).

Example 8

(+)-3β-(Acetoxymethyl)-4β-(4-chlorophenyl)-1-melthylpiperidine (8).

Using a procedure similar to that described in Example 7, except replacing compound 5 used therein with compound 6, the title compound 8 was prepared (93%) as a white solid: [α]$^{25}_D$ +107° (c 0.35; EtOH); MS m/z (%) 281 (M$^+$, 6).

Example 9

(−) 4β-(4-chlorophenyl)-1-methyl-3β-n-propylpiperidine (9).

Oxalyl chloride (0.19 mL) was dissolved in anhydrous CH$_2$Cl$_2$ (15 mL), and the solution was cooled to −78° C. Dimethyl sulfoxide (0.32 mL) was added, after 5 minutes, alcohol 5 (0.5 g, 2.08 mmol) was added in CH$_2$Cl$_2$ (5 mL), and stirring was continued for 30 minutes. The reaction mixture was quenched by adding Et$_3$N (2.84 mL), and the resulting solution was warmed to room temperature, diluted with CH$_2$Cl$_2$ (30 mL), washed with NH$_4$Cl (2×30 mL), dried, and concentrated under reduced pressure to provide the intermediate aldehyde (0.45 g, 91%) as a colorless oil used in the next step without further purification: $^1$H NMR (CDCl$_3$) δ1.9–2.0 (m, 1H), 2.10 (dt, 1H, J=2.4 and 11.4 Hz), 2.29 (s, 3H), 2.2–2.4 (m, 2H), 2.64–2.74 (m, 1H), 2.92 (dt, 1H, J=3.9 and 12.9 Hz), 3.0–3.1 (m, 1H), 3.28 (br d, 1H, J=11.4 Hz), 7.2 (d, 2H, J=8.4 Hz), 7.29 (d, 2H, J=8.4 Hz), 8.7 (s, 1H), $^{13}$C NMR (CDCl$_3$) δ 27.2, 40.9, 46.5, 51.9, 55.9, 57.0, 128.6, 128.7, 132.3, 140.6, 203.9.

A solution of n-BuLi (2.28 mL, 1 M in hexane, 5.7 mmol) was dissolved in THF (10 mL) and cooled to 0° C. Ethyltriphenylphosphonium bromide (2.1 g, 5.7 mmol) was added slowly under nitrogen. The resulting yellow-orange solution was stirred at 0° C. for 30 minutes, and the cooling bath was removed. The crude aldehyde (0.45 g, 1.9 mmol) was added in THF (2 mL), and the reaction mixture was stirred for 15 hours at room temperature, diluted with EtOAc (20 mL), and washed with a saturated solution of NH$_4$Cl (2×30 mL). The organic phase was extracted with 10% HCl (3×10 mL). The combined aqueous phases were washed with EtOAc (30 mL), neutralized with a saturated solution of NaHCO$_3$, and extracted with CH$_2$Cl$_2$ (2×30 mL). The combined organic phases were dried and concentrated under reduced pressure, and the residue was purified by flash chromatography on silica gel using ether/Et$_3$N 9.5/0.5 as eluent to afford an olefin intermediate as a mixture of cis and trans isomers (0.3 g, 63%): MS m/z (%) 248 (M$^+$, 6), 57 (100).

To a solution of the olefins (0.2 g, 0.80 mmol) in cyclohexane (20 mL) was added 5% Pt/C (0.2 g). The mixture was stirred at room temperature for 30 minutes under H$_2$ (40 psi).

The solution was filtered over celite and evaporated to dryness. The resulting colorless oil was purified by flash chromatography on silica gel using ether/Et$_3$N 9.5/0.5 as eluent to afford the title compound 9 (0.19 g, 94%) as a colorless oil: $[\alpha]^{25}_D$ −84° (c 0.5, EtOH); $^1$H NMR (benzene-d$_6$) δ 0.71 (t, 3H, J=6.9 Hz), 0.75–1.0 (m, 2H), 1.2–1.4 (m, 2H), 1.52–1.65 (m, 1H), 1.65–1.84 (m, 2H), 1.84–2.0 (m, 2H), 2.14 (s, 3H), 2.47 (dt, 1H, J=3.6 and 12.3 Hz), 2.7–2.84 (m, 1H), 6.77 (d, 2H, J=8.4 Hz), 7.15 (d, 2H, J=8.4 Hz); $^{13}$C NMR. (CDCl$_3$) δ 14.0, 21.1, 25.4, 27.6, 40.2, 43.9, 46.8, 56.5, 59.4, 128.1, 128.8, 131.4. 142.9; MS m/z (%) 251 (M$^+$, 8), 208 (8), 112 (24), 44 (100).

The hydrochloride salt was prepared by dissolution of the free base in a methanolic solution of HCl(g), concentration, and final trituration of the crude salt with ether: mp>230° C.; $[\alpha]^{25}_D$ −73° (c 0.25, EtOH); $^1$H NMR (methanol-d$_4$) δ 0.78 (t, 3H, J=6.6 Hz), 0.9–1.1 (m, 2H), 1.28–1.5 (m, 2H), 1.94–2.06 (m, 1H), 2.14–2.38 (m, 2H), 2.92 (s, 31), 3.04–3.4 (m, 3H), 3.54–3.7 (m, 2H), 7.24 (d, 2H, J=7.8 Hz), 7.35 (d, 2H, J=7.8 Hz).

Example 10

(−)-Methyl 1-Methyl-4β-phenylpiperidine-3β-carboxylate (10).

A mixture of compound 3 (0.7 g, 2.61 mmol) and 10% Pd/C (0.28 g) in MeOH (20 mL) was hydrogenated under 1 atm of H$_2$ for 3 hours. The resulting mixture was filtered over celite and evaporated to dryness. The resulting pale yellow oil was purified by flash chromatography on silica gel using ether/Et$_3$N 9.5/0.5 as eluent to afford the title compound (0.6 g, 98%) as a colorless oil: $[\alpha]^{25}_D$ −54° (c 1; EtOH); $^1$H NMR (CDCl$_3$) δ 1.76–1.9 (m, H$_{5eq}$), 2.09 (dt, H$_{6ax}$, J=2.7 and 11.1 Hz), 2.29 (s, 3H), 2.37 (dd, H$_{2'}$, J=3.6 and 11.7 Hz), 2.70 (dq, H$_{5ax}$, J=3.9 and 12.3 Hz), 2.85 (dt, H$_4$, J=3.9 and 11.7 Hz), 2.92–3.06 (m, H$_3$ and H$_{6eq}$), 3.18 (br d, H$_{2''}$, J=12.0 Hz), 3.50 (s, 3H), 7.1–7.4 (m, 5H); $^{13}$C NMR (CDCl$_3$) δ 26.6, 41.8, 46.2, 46.6, 51.2, 55.9, 58.3, 126.1, 127.6, 128.0, 143.0, 172.7; MS m/z (%) 233 (M$^+$, 13), 232 (6), 174 (17), 70 (26), 44 (100).

The hydrochloride salt was prepared by dissolution of the free base in a methanolic solution of HCl(g), concentration, and final trituration of the crude salt with ether:$[\alpha]^{25}_D$ −130° (c 1.0, EtOH); mp 168–169° C.; $^1$H NMR (methanol-d$_4$) δ 2.0–2.1 (m, 1H), 2.5–2.7 (m, 1H), 2.95 (s, 3H), 3.1–3.5 (m, 4H), 3.42 (s, 3H), 3.6–3.7 (m, 2H), 3.7–3.85 (m, 1H), 7.2–7.4 (m, 5H).

Example 11

(+)-Methyl 4β-(4-chlorophenyl)-1-methylpiperidine-3α-carboxylate (11).

To a solution of compound 3 (0.5 g, 1.87 mmol) in MeOH (6 mL) was added a 30% methanolic solution of sodium methoxide (0.04 mL). The resulting solution was stirred at reflux for 24 hours and concentrated under reduced pressure. CH$_2$Cl$_2$ and brine were added, and the organic layer was washed with brine. Concentration of the combined organic phase afforded compound 3 and compound 11 in a 1:32 ratio (determined by GC-MS analysis). Purification of the crude product by silica gel flash chromatography using ether/Et$_3$N 9.8/0.2 as eluent afforded the title compound (0.43 g, 86%) as a colorless oil: $[\alpha]^{25}_D$ +46° (c 1.0, EtOH).

The hydrochloride salt was prepared by dissolution of the free base in a methanolic solution of HCl(g), resulting in a direct crystallization of the desired salt: $[\alpha]^{25}_D$ +55° (c 0.5, EtOH); mp>230° C.

Example 12

(−)-Methyl 4β-(4-Chlorophenyl)-1-methylpipericline-3α-carboxylate (12).

To a solution of compound 4 (0.4 g, 1.49 mmol) in MeOH (3 mL) was added a 30% methanolic solution of sodium methoxide (0.01 mL). The resulting solution was stirred at reflux for 11 hours and concentrated under reduced pressure. CH$_2$Cl$_2$ and a saturated solution of NH$_4$Cl were added. The organic layer was washed with brine, dried over sodium sulfate, and concentrated under reduced pressure to afford compounds 4 and 12 in a 1:5.6 ratio (determined by GC-MS analysis). Purification of the crude product by silica gel flash chromatography using ether/Et$_3$N 9.8/0.2 as eluent afforded the title compound (0.35 g, 85%) as a colorless oil: $[\alpha]^{25}_D$ −50° (c 1.0, EtOH).

Example 13

(+)-4β-(4Cchlorophenyl)-3α-(hydroxymethyl)-1-methylpiperidine (13).

Using a procedure similar to that described in Example 5, except replacing the compound 3 used therein with compound 11, the title compound was obtained (84%) as a colorless oil: $[\alpha]^{25}_D$ +38° (c 0.5; EtOH); nip 148–150° C.; $^1$H NMR (CDCl$_3$) δ 1.4 (br s, OH), 1.7–2.1 (m, 5H), 2.29 (dd, 1H, J=5.4 and 10.5 Hz), 2.36 (s, 3H), 2.95 (d, 1H, J=10.8 Hz), 3.15 (d, 1H, J=10.8 Hz), 3.24 (dd, 1H, J=6.6 and 10.8 Hz), 3.41 (dd, 1H, J=3.0 and 10.8 Hz), 7.14 (d, 2H, J=8.4 Hz), 7.27 (d, 2 H, J:=8.4 Hz).

Example 14

(+)-3β-(Acetoxymethyl)-4β-(4-chlorophenyl)-1-methylpiperidine (14).

Using a procedure similar to that described in Example 7, except replacing compound 5 used therein with compound 13, the title compound was obtained (80%) as a white solid: $^1$H NMR (CDCl$_3$) δ 1.7–1.9 (m, 3H), 1.97 (s, 3H), 1.95–2.1 (m, 1H), 2.1–2.3 (m, 2H), 2.35 (s, 3H), 2.95 (d, 1H, J=11.4 Hz), 3.07 (d, 1H, J=9.6 Hz), 3.63 (dd, 1H, J=7.5 and 11.4 Hz), 3.82 (dd, 1H, J=3.0 and 11.1 Hz), 7.12 (d, 2H, J=8.4 Hz), 7.27 (d, 2H, J=8.4 Hz); $^{13}$C NMR (CDCl$_3$) δ 20.7, 34.4, 41.0, 44.2, 46.4, 56.0, 59.3, 65.2, 128.7, 128.8, 132.2, 142.1, 170.9.

Example 15

(+) 4β-(4-chlorophenyl)-1-methyl-3α-n-propylpiperidine (15).

Using a procedure similar to that described in Example 9, except replacing compound 5 used therein with compound 13, the title compound was obtained (70%) as a colorless oil: $[\alpha]^{25}_D$ +418 (c 1.0, EtOH); $^1$H NMR (CDCl$_3$) δ 0.73 (t, 3H, J=7.2 Hz), 0.8–1.0 (m, 1H), 1.0–1.2 (m, 2H), 1.2–1.4 (m, 1H), 1.65 (t, 1H, J=10.8 Hz), 1.7–1.9 (m, 3H), 1.9–2.15 (m, 2H), 2.32 (s, 3H), 2.93 (d, 1H, J=11.1 Hz), 3.05 (d, 1H, J=10.8 Hz), 7.10 (d, 2H, J=8.4 Hz), 7.25 (d, J=8.1 Hz); $^{13}$C NMR (CDCl$_3$) d 14.1, 19.7, 33.9, 35.0, 40.8, 46.5, 48.2, 56.3, 61.6, 128.5, 129.0, 131.6, 143.8.

The hydrochloride salt was prepared by dissolution of the free base in a methanolic solution of HCl(g), concentration, and final trituration of the crude salts with ether: $[\alpha]^{25}_D$ +348 (c 0.25, EtOH); mp 216° C. (EtOhnc); $^1$H NMR (methanol-d$_4$) δ 0.77 (t, 3H, J=6.9 Hz), 1.0–1.4 (m, 4H), 1.9–2.2 (m, 3H), 2.56 (q, 1H, J=10.8 Hz), 2.86 (t, 1H, J=12.6 Hz), 2.93 (s, 3H), 3.0–3.2 (m, 1H), 3.5–3.7 (m, 2H), 7.23 (d, 2H, J=8.4 Hz), 7.35 (d, 2H, J=8.4 Hz).

Example 16

The following illustrate representative phannaceutical dosage forms, containing a compound of formula I ('Compound X'), for therapeutic or prophylactic use in humans.

| (i) Tablet 1 | mg/tablet |
|---|---:|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---:|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---:|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---:|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0–7.5) | q.s. |
| Water for injection | q.s. ad 1 mL |

| (v) Injection 2 (10 mg/ml) | mg/ml |
|---|---:|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |

| (vi) Aerosol | mg/can |
|---|---:|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

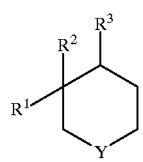

(I)

wherein
Y is $NR^6$;
$R^1$ is —$C(O)OR_a$, cyano, $(C_1-C_6)$alkyl, $(C_1-C_6)$alkanoyl, $(C_2-C_6)$alkenyl, or $(C_2-C_6)$alkynyl, wherein any instance of $R_1$ which is $(C_1-C_6)$alkyl, $(C_1-C_6)$alkanoyl, $(C_2-C_6)$alkenyl, or $(C_2-C_6)$alkynyl may optionally be substituted by 1, 2 or 3 Z, wherein each Z is independently chloro, bromo, iodo, nitro, cyano, $(C_2-C_6)$acyloxy, $C(O)OR_b$, $C(O)NR_cR_d$, or $S(O)_nR_g$; and $R^3$ is phenyl, $(C_{10})$aryl, $(C_6-C_{10})$aryl$(C_1-C_6)$alkyl, or $(C_6-C_{10})$arylcarbonyl, wherein any phenyl substituent is substituted with 1, 2, or 3 instances of Z, and any other $(C_6-C_{10})$aryl substituent may optionally be substituted on carbon by 1, 2 or 3 Z; or
$R^1$ is —$CH_2$—, or —$CH_2CH_2$—, wherein $R^1$ is attached to a carbon at the ortho position of $R^3$; and $R^3$ is $(C_6-C_{10})$aryl;
$R^2$ is hydrogen or $(C_1-C_6)$alkyl;
$R^6$ is hydrogen, $(C_1-C_6)$alkyl, $(C_1-C_6)$alkanoyl, or $S(O)_2R_h$;
n is 0, 1 or 2;
$R_a$ to $R_g$ are independently hydrogen or $(C_1-C_4)$alkyl; and
$R_h$ is H, $(C_1-C_4)$alkyl, or phenyl; or a pharmaceutically acceptable salt thereof.

2. A compound of formula I:

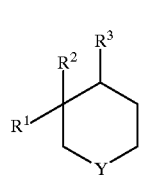

(I)

wherein
Y is $NR^6$;
$R^1$ is cyano, $(C_1-C_6)$alkyl, $(C_1-C_6)$alkanoyl, $(C_2-C_6)$alkenyl, or $(C_2-C_6)$alkynyl, wherein any instance of $R_1$ which is $(C_1-C_6)$alkanoyl, $(C_2-C_6)$alkenyl, or $(C_2-C_6)$alkynyl may optionally be substituted by 1, 2 or 3 Z, wherein each Z is independently halo, nitro, cyano, hydroxy, $(C_1-C_6)$alkoxy, $(C_2-C_6)$acyloxy, $C(O)OR_b$, $C(O)NR_cR_d$, $NR_eR_f$, or $S(O)_nR_g$; and $R^3$ is phenyl, $(_{10})$aryl, $(C_6-C_{10})$aryl$(C_1-C_6)$alkyl, or $(C_6-C_{10})$arylcarbonyl, wherein any phenyl substituent is substituted with 1, 2, or 3 instances of Z, and any other $(C_6-C_{10})$aryl substituent may optionally be substituted on carbon by 1, 2 or 3 Z; or
$R^1$ is —$CH_2$—, or —$CH_2CH_2$—, wherein $R^1$ is attached to a carbon at the ortho position of $R^3$; and $R^3$ is $(C_6-C_{10})$aryl;
$R^2$ is hydrogen or $(C_1-C_6)$alkyl;
$R^6$ is hydrogen, $(C_1-C_6)$alkyl, $(C_1-C_6)$alkanoyl, or $S(O)_2R_h$;

n is 0, 1 or 2;

$R_a$ to $R_g$ are independently hydrogen or $(C_1-C_4)$alkyl; and $R_h$ is H, $(C_1-C_4)$alkyl, or phenyl; or a pharmaceutically acceptable salt thereof.

3. The compound of claim 1, wherein $R^3$ is $(C_6-C_{10})$aryl, $(C_6-C_{10})$aryl$(C_1-C_6)$alkyl, $(C_6-C_{10})$arylcarbonyl, wherein any aryl substituent may optionally be substituted on carbon by 1, 2 or 3 Z; or $R^1$ is —CH$_2$—, or —CH$_2$CH$_2$—, wherein $R^1$ is attached to a carbon at the ortho position of $R^3$; and $R^3$ is $(C_6-C_{10})$aryl.

4. The compound of claim 1, wherein $R^1$ is —C(O)OR$_a$, cyano, $(C_1-C_6)$alkyl $(C_2-C_6)$alkenyl, or $(C_2-C_6)$alkynyl.

5. The compound of claim 1, wherein $R^1$ is $(C_1-C_6)$alkyl, $(C_2-C_6)$alkenyl, or $(C_2-C_6)$alkynyl.

6. The compound of claim 1, wherein $R^1$ is $(C_1-C_6)$alkyl.

7. The compound of claim 1, wherein $R^1$ is —C(O)OR$_a$; and $R_a$ is $(C_1-C_4)$alkyl.

8. The compound of claim 1 or 2, wherein $R^2$ is hydrogen.

9. The compound of claim 1 or 2, wherein $R^3$ is phenyl, $(C_{10})$aryl, $(C_6-C_{10})$aryl$(C_1-C_6)$alkyl, or $(C_6-C_{10})$arylcarbonyl, wherein any phenyl substituent is substituted with 1, 2, or 3 instances of Z, and any other $(C_6-C_{10})$aryl substituent may optionally be substituted on carbon by 1, 2 or 3 Z.

10. The compound of claim 1, 2, or 8, wherein $R^3$ is 4-chlorophenyl, 4-methylphenyl, or 4-isopropenylphenyl.

11. The compound of claim 1 or 2, wherein $R^6$ is hydrogen, $(C_1-C_6)$alkyl or $(C_1-C_6)$alkanoyl.

12. The compound of claim 1, wherein $R^1$ is methoxycarbonyl, $(C_1-C_6)$alkyl, or acetoxymethyl; $R^2$ is hydrogen; and $R^3$ is 4-chlorophenyl, 4-methylphenyl, or 4-isopropenylphenyl; and $R^6$ is methyl.

13. The compound of claim 1, 2, or 4, wherein the stereochemical relationship between $R^1$ and $R^3$ is trans.

14. The compound of claim 1, which is trans-1-methyl-4-(4-chlorophenyl)piperidine-3-carboxylic acid methyl ester.

15. The compound of claim 1, which is (+)-methyl 4-(4-chlorophenyl)-1-methylpiperidine-3-carboxylate.

16. The compound of claim 1, which is (−) 4-(4-chlorophenyl)-1-methyl-3-n-propylpiperidine; or (+) 4-(4-chlorophenyl)-1-methyl-3-n-propylpiperidine.

17. A pharmaceutical compositions comprising a compound of claim 1 or 2, or a pharmaceutically acceptable salt thereof; and a pharmaceutically acceptable diluent or carrier.

* * * * *

UNITED STATES PATENT AND TRADEMARK OFFICE
CERTIFICATE OF CORRECTION

PATENT NO. : 6,180,648 B1
DATED : January 30, 2001
INVENTOR(S) : Alan P. Kozikowski and Gian Luca Araldi It is certified that error appears in the above-identified patent and that said Letters Patent is hereby corrected as shown below:

<u>Title page,</u>
Item [73], "Assignee", replace "Biostream Therapeutics, Inc., Cambridge, MA (US)" with -- Georgetown University, Washington, DC (US) --.

Signed and Sealed this

Thirtieth Day of July, 2002

Attest:

JAMES E. ROGAN
*Attesting Officer*   *Director of the United States Patent and Trademark Office*